(12) United States Patent
Moore et al.

(10) Patent No.: US 10,729,672 B2
(45) Date of Patent: Aug. 4, 2020

(54) ANTINEOPLASTIC COMBINATIONS WITH MTOR INHIBITOR, TRASTUZUMAB AND/OR HKI-272

(71) Applicant: Wyeth LLC, Madison, NJ (US)

(72) Inventors: Laurence Moore, Newton, MA (US); Charles Zacharchuk, Westford, MA (US); Sridhar K. Rabindran, Chestnut Ridge, NY (US)

(73) Assignee: Wyeth LLC, New York, NY (US)

( * ) Notice: Subject to any disclaimer, the term of this patent is extended or adjusted under 35 U.S.C. 154(b) by 104 days.

(21) Appl. No.: 13/874,147

(22) Filed: Apr. 30, 2013

(65) Prior Publication Data

US 2014/0050721 A1    Feb. 20, 2014

Related U.S. Application Data

(60) Continuation of application No. 13/454,768, filed on Apr. 24, 2012, now abandoned, which is a continuation of application No. 12/539,914, filed on Aug. 12, 2009, now abandoned, which is a division of application No. 11/592,066, filed on Nov. 2, 2006, now abandoned.

(60) Provisional application No. 60/837,509, filed on Aug. 14, 2006, provisional application No. 60/733,562, filed on Nov. 4, 2005.

(51) Int. Cl.
| | | |
|---|---|---|
| *A61K 31/337* | (2006.01) | |
| *A61K 31/436* | (2006.01) | |
| *A61K 31/4709* | (2006.01) | |
| *A61K 45/06* | (2006.01) | |
| *A61K 31/4745* | (2006.01) | |
| *A61K 39/395* | (2006.01) | |

(52) U.S. Cl.
CPC .......... *A61K 31/337* (2013.01); *A61K 31/436* (2013.01); *A61K 31/4709* (2013.01); *A61K 31/4745* (2013.01); *A61K 39/39558* (2013.01); *A61K 45/06* (2013.01)

(58) Field of Classification Search
None
See application file for complete search history.

(56) References Cited

U.S. PATENT DOCUMENTS

| | | |
|---|---|---|
| 4,966,891 A | 10/1990 | Fujiu et al. |
| 5,362,718 A | 11/1994 | Skotnicki et al. |
| 5,453,497 A | 9/1995 | Kamiya et al. |
| 5,472,949 A | 12/1995 | Arasaki et al. |
| 5,476,932 A | 12/1995 | Brinkman et al. |
| 5,715,151 A | 1/1998 | Dow et al. |
| 5,760,041 A | 6/1998 | Wissner et al. |
| 6,002,008 A | 12/1999 | Wissner et al. |
| 6,143,764 A | 11/2000 | Kubo et al. |
| 6,251,912 B1 | 6/2001 | Wissner et al. |
| 6,277,983 B1 | 8/2001 | Shaw et al. |
| 6,288,082 B1 | 9/2001 | Wissner et al. |
| 6,297,258 B1 | 10/2001 | Wissner et al. |
| 6,384,051 B1 | 5/2002 | Frost et al. |
| 6,387,371 B1 | 5/2002 | Hudziak et al. |
| 6,399,063 B1 | 6/2002 | Hudziak et al. |
| 6,432,979 B1 | 8/2002 | Frost et al. |
| 6,511,986 B2 | 1/2003 | Zhang et al. |
| 6,617,333 B2 | 9/2003 | Rabindran et al. |
| 6,780,996 B2 | 8/2004 | Boschelli et al. |
| 6,821,515 B1 | 11/2004 | Cleland et al. |
| 6,821,988 B2 | 11/2004 | Wissner et al. |
| 7,026,330 B2 | 4/2006 | Grupp et al. |
| 7,091,213 B2 | 8/2006 | Metcalf et al. |
| 7,126,025 B2 | 10/2006 | Considine et al. |
| 7,189,735 B2 | 3/2007 | Dukart et al. |
| 7,235,564 B2 | 6/2007 | Scott et al. |
| 7,294,468 B2 | 10/2007 | Bell et al. |
| 7,297,795 B2 | 11/2007 | Sutherland et al. |
| 7,306,801 B2 | 12/2007 | Caligiuri et al. |
| RE40,418 E | 7/2008 | Rabindran et al. |
| 7,399,865 B2 | 7/2008 | Wissner et al. |
| 7,846,936 B2 | 12/2010 | Hilberg et al. |
| 7,897,159 B2 | 3/2011 | Weber |
| 7,915,402 B2 | 3/2011 | Anderson et al. |
| 7,943,778 B2 | 5/2011 | Jiang et al. |
| 7,964,349 B2 | 6/2011 | Bell et al. |
| 7,982,043 B2 | 7/2011 | Wissner et al. |

(Continued)

FOREIGN PATENT DOCUMENTS

| | | |
|---|---|---|
| CN | 1437942 A | 8/2003 |
| CN | 101185633 A | 5/2008 |

(Continued)

OTHER PUBLICATIONS

Chan, "Targeting the mammalian target of rapamycin (mTOR): a new approach to treating cancer", Br. J. Cancer, 2004, published online Sep. 14, 2004, vol. 91, pp. 1420-1424 (Year: 2004).*
Mondesire et al., Clin. Cancer Res., Oct. 15, 2004, vol. 10, pp. 7031-7042 (Year: 2004).*
Lynch et al., "Summary Statement: Novel Agents in the Treatment of Lung Cancer: Advances in Epidermal Growth Factor Receptor-Targeted Agents", Clin. Cancer Res., 2006, vol. 12, pp. 4365s-4371s (Year: 2006).*
Abrams, et al., Preclinical Evaluation of the Tyrosine Kinase inhibitor SU11248 as a Single Agent and in Combination with "standard of care" Therapeutic Agents for the Treatment of Breast Cancer, Molecular Cancer Therapeutics, Oct. 2003, 2(1): 1011-1021.

(Continued)

*Primary Examiner* — James D. Anderson
*Assistant Examiner* — Stephanie K Springer
(74) *Attorney, Agent, or Firm* — Jones Day

(57) ABSTRACT

A combination of temsirolimus and trastuzumab in the treatment of cancer is provided. A combination of temsirolimus and HKI-272 is provided. A combination of a trastuzumab and a HKI-272 is also provided. Regimens and kits for treatment of metastatic breast cancer, containing trastuzumab, temsirolimus and/or HKI-272, optionally in combination with other anti-neoplastic agents, or immune modulators are described.

14 Claims, 3 Drawing Sheets

(56) References Cited

U.S. PATENT DOCUMENTS

| | | |
|---|---|---|
| 8,022,216 B2 | 9/2011 | Lu et al. |
| 8,105,769 B2 | 1/2012 | Bell et al. |
| 8,173,814 B2 | 5/2012 | Lu et al. |
| 8,338,456 B2 | 12/2012 | Coughlin et al. |
| 8,394,959 B2 | 3/2013 | Lu et al. |
| 8,465,916 B2 | 6/2013 | Bell et al. |
| 8,518,446 B2 | 8/2013 | Asraf et al. |
| 8,524,281 B2 | 9/2013 | Venkata Ramana Rao et al. |
| 8,669,273 B2 | 3/2014 | Zacharchuk et al. |
| 8,790,708 B2 | 7/2014 | Asraf et al. |
| 2002/0002162 A1 | 1/2002 | Lee |
| 2002/0183239 A1 | 12/2002 | Gibbons, Jr. et al. |
| 2002/0183240 A1 | 12/2002 | Gibbons et al. |
| 2002/0198137 A1 | 12/2002 | Dukart et al. |
| 2002/0198317 A1 | 12/2002 | Dukart et al. |
| 2003/0144252 A1 | 7/2003 | Furr |
| 2003/0149056 A1 | 8/2003 | Wissner et al. |
| 2003/0153593 A1 | 8/2003 | Dukart et al. |
| 2004/0039010 A1 | 2/2004 | Grupp et al. |
| 2004/0162442 A1 | 8/2004 | Considine et al. |
| 2004/0176339 A1 | 9/2004 | Sherman et al. |
| 2004/0209930 A1 | 10/2004 | Carboni et al. |
| 2004/0258662 A1 | 12/2004 | Gibbons et al. |
| 2005/0025825 A1 | 2/2005 | Heasley et al. |
| 2005/0032825 A1 | 2/2005 | Metcalf et al. |
| 2005/0038080 A1 | 2/2005 | Boyer et al. |
| 2005/0043233 A1 | 2/2005 | Stefanic et al. |
| 2005/0059678 A1 | 3/2005 | Wissner et al. |
| 2005/0129761 A1 | 6/2005 | Venkata Ramana Rao et al. |
| 2005/0136063 A1 | 6/2005 | Wang et al. |
| 2005/0187184 A1 | 8/2005 | Gibbons et al. |
| 2005/0272083 A1 | 12/2005 | Seshagiri |
| 2005/0272758 A1 | 12/2005 | Bayever et al. |
| 2006/0030547 A1 | 2/2006 | Dukart et al. |
| 2006/0035904 A1 | 2/2006 | Gibbons et al. |
| 2006/0058311 A1 | 3/2006 | Munzert et al. |
| 2006/0079515 A1 | 4/2006 | Frost |
| 2006/0084666 A1 | 4/2006 | Harari et al. |
| 2006/0094674 A1 | 5/2006 | Neel et al. |
| 2006/0128793 A1 | 6/2006 | Zask et al. |
| 2006/0147959 A1 | 7/2006 | Bell et al. |
| 2006/0178387 A1 | 8/2006 | Fujimoto/Ouchi et al. |
| 2006/0235046 A1 | 10/2006 | Zacharchuk et al. |
| 2006/0270668 A1 | 11/2006 | Chew et al. |
| 2006/0270669 A1 | 11/2006 | Chew et al. |
| 2007/0014859 A1 | 1/2007 | Shah et al. |
| 2007/0104721 A1 | 5/2007 | Moore et al. |
| 2007/0105887 A1 | 5/2007 | Moore |
| 2007/0281932 A1 | 12/2007 | Bernier et al. |
| 2008/0096212 A1 | 4/2008 | Bell et al. |
| 2008/0112888 A1 | 5/2008 | Wang |
| 2008/0166359 A1 | 7/2008 | Lamb |
| 2008/0193448 A1 | 8/2008 | Baum |
| 2008/0207615 A1 | 8/2008 | Bell et al. |
| 2008/0234264 A1 | 9/2008 | Bell et al. |
| 2008/0254040 A1 | 10/2008 | Stefanic et al. |
| 2008/0268034 A1 | 10/2008 | Karanth et al. |
| 2008/0286771 A1 | 11/2008 | Hudson et al. |
| 2008/0286785 A1 | 11/2008 | Nishio et al. |
| 2009/0035269 A1 | 2/2009 | Weber |
| 2009/0047278 A1 | 2/2009 | Owa et al. |
| 2009/0060873 A1 | 3/2009 | Sporn et al. |
| 2009/0176827 A1 | 7/2009 | Lu et al. |
| 2009/0203709 A1 | 8/2009 | Steinberg et al. |
| 2009/0246198 A1 | 10/2009 | Dong et al. |
| 2009/0297519 A1 | 12/2009 | Moore et al. |
| 2009/0306101 A1 | 12/2009 | Solca et al. |
| 2009/0312360 A1 | 12/2009 | Zacharchuk |
| 2009/0317456 A1 | 12/2009 | Karrasch et al. |
| 2009/0318480 A1 | 12/2009 | Solca |
| 2009/0325877 A1 | 12/2009 | Grunt et al. |
| 2010/0041904 A1 | 2/2010 | Jiang et al. |
| 2010/0048540 A1 | 2/2010 | Boyle et al. |
| 2010/0048892 A1 | 2/2010 | Anderson et al. |
| 2010/0056777 A1 | 3/2010 | Anderson et al. |
| 2010/0069340 A1 | 3/2010 | Zacharchuk et al. |
| 2010/0081632 A1 | 4/2010 | Oksenberg et al. |
| 2010/0087482 A1 | 4/2010 | Haber et al. |
| 2010/0092490 A1 | 4/2010 | Uenaka et al. |
| 2010/0105031 A1 | 4/2010 | Matsui et al. |
| 2010/0113474 A1 | 5/2010 | Zacharchuk et al. |
| 2010/0120072 A1 | 5/2010 | Lorence et al. |
| 2010/0120768 A1 | 5/2010 | Steinberg et al. |
| 2010/0143340 A1 | 6/2010 | Kolhe et al. |
| 2010/0143350 A1 | 6/2010 | Green et al. |
| 2010/0166744 A1 | 7/2010 | Wong |
| 2010/0189773 A1 | 7/2010 | Mortimore et al. |
| 2010/0226943 A1 | 9/2010 | Brennan et al. |
| 2010/0297118 A1 | 11/2010 | Macdougall et al. |
| 2010/0298760 A1 | 11/2010 | Olle et al. |
| 2010/0310503 A1 | 12/2010 | Li et al. |
| 2011/0014117 A1 | 1/2011 | Wang et al. |
| 2011/0045459 A1 | 2/2011 | Mischel et al. |
| 2011/0052570 A1 | 3/2011 | Klagsbrun et al. |
| 2011/0091421 A1 | 4/2011 | Mann |
| 2011/0091524 A1 | 4/2011 | Wang et al. |
| 2011/0097340 A1 | 4/2011 | Ramachandra et al. |
| 2011/0104256 A1 | 5/2011 | Wang et al. |
| 2011/0111018 A1 | 5/2011 | Asraf et al. |
| 2011/0112180 A1 | 5/2011 | Jiang et al. |
| 2011/0129456 A1 | 6/2011 | Wang et al. |
| 2011/0165257 A1 | 7/2011 | Rao et al. |
| 2012/0071507 A1 | 3/2012 | Berkenblit et al. |
| 2012/0270896 A1 | 10/2012 | Zacharchuk |
| 2012/0308560 A1 | 12/2012 | Moore et al. |
| 2013/0189274 A1 | 7/2013 | Berkenblit et al. |
| 2013/0281488 A1 | 10/2013 | Lu et al. |
| 2013/0316935 A1 | 11/2013 | Bell et al. |
| 2014/0004203 A1 | 1/2014 | Rao et al. |
| 2014/0050721 A1 | 2/2014 | Moore et al. |
| 2014/0171384 A1 | 6/2014 | Zacharchuk et al. |

FOREIGN PATENT DOCUMENTS

| | | |
|---|---|---|
| EP | 0693285 A2 | 1/1996 |
| EP | 1448531 B1 | 8/2007 |
| EP | 1663978 B1 | 11/2007 |
| EP | 1854463 A1 | 11/2007 |
| EP | 1978106 A1 | 10/2008 |
| EP | 1951274 B1 | 12/2009 |
| EP | 1848414 B1 | 4/2011 |
| EP | 1859793 B1 | 4/2011 |
| JP | 2003-519698 A | 6/2003 |
| JP | 2007-145745 A | 6/2007 |
| WO | WO 1992/22653 | 12/1992 |
| WO | WO 1995/28406 | 10/1995 |
| WO | WO 1996/33978 A1 | 10/1996 |
| WO | WO 1996/33980 A1 | 10/1996 |
| WO | WO 1998/43960 A1 | 10/1998 |
| WO | WO 2000/018761 A1 | 4/2000 |
| WO | WO 2001/023395 | 4/2001 |
| WO | WO 2001/051919 A2 | 7/2001 |
| WO | WO 2002/080975 | 10/2002 |
| WO | WO 2002/098416 | 12/2002 |
| WO | WO 2002/102976 A2 | 12/2002 |
| WO | WO 2003/050090 A1 | 6/2003 |
| WO | WO 2003/103676 A2 | 12/2003 |
| WO | WO 2004/004644 | 1/2004 |
| WO | WO 2004/066919 A2 | 8/2004 |
| WO | WO 2004/078133 | 9/2004 |
| WO | WO 2004/093854 | 11/2004 |
| WO | WO 2004/096224 A2 | 11/2004 |
| WO | WO 2005/018677 A2 | 3/2005 |
| WO | WO 2005/032513 A2 | 4/2005 |
| WO | WO 2005/034955 A1 | 4/2005 |
| WO | WO 2005/037287 A1 | 4/2005 |
| WO | WO 2005/044091 A2 | 5/2005 |
| WO | WO 2005/049021 | 6/2005 |
| WO | WO 2005/087265 | 9/2005 |
| WO | 2005/094357 A2 | 10/2005 |
| WO | WO 2006/044453 | 4/2006 |
| WO | WO 2006/044748 A2 | 4/2006 |
| WO | WO 2006/081985 A1 | 8/2006 |
| WO | WO 2006/084058 A2 | 8/2006 |

(56) References Cited

FOREIGN PATENT DOCUMENTS

| | | |
|---|---|---|
| WO | WO 2006/095185 | 9/2006 |
| WO | WO 2006/098978 A1 | 9/2006 |
| WO | 2006/113304 A2 | 10/2006 |
| WO | WO 2006/113151 | 10/2006 |
| WO | WO 2006/116514 A2 | 11/2006 |
| WO | WO 2006/0120557 | 11/2006 |
| WO | WO 2006/120573 A2 | 11/2006 |
| WO | WO 2006/127205 A2 | 11/2006 |
| WO | WO 2006/127207 A1 | 11/2006 |
| WO | WO 2007/000234 A1 | 1/2007 |
| WO | WO 2007/011619 A2 | 1/2007 |
| WO | WO 2007/056118 A1 | 5/2007 |
| WO | WO 2007/075794 A2 | 7/2007 |
| WO | WO 2007/095038 A2 | 8/2007 |
| WO | 2007/116025 A2 | 10/2007 |
| WO | WO 2007/130438 A2 | 11/2007 |
| WO | WO 2007/137187 A2 | 11/2007 |
| WO | WO 2007/139797 A2 | 12/2007 |
| WO | WO 2008/076143 A1 | 6/2008 |
| WO | WO 2008/076278 A2 | 6/2008 |
| WO | WO 2008/089087 A2 | 7/2008 |
| WO | WO 2008/093878 A1 | 8/2008 |
| WO | WO 2008/121467 A2 | 10/2008 |
| WO | WO 2008/127710 A2 | 10/2008 |
| WO | WO 2008/130910 A1 | 10/2008 |
| WO | WO 2009/036099 A1 | 3/2009 |
| WO | WO 2009/042613 A1 | 4/2009 |
| WO | WO 2009/052264 A2 | 4/2009 |
| WO | WO 2009/061349 A1 | 5/2009 |
| WO | WO 2009/105234 A2 | 8/2009 |
| WO | WO 2009/108637 A1 | 9/2009 |
| WO | WO 2009/111073 A2 | 9/2009 |
| WO | WO 2009/121031 A1 | 10/2009 |
| WO | WO 2009/126662 A1 | 10/2009 |
| WO | WO 2009/129545 A1 | 10/2009 |
| WO | WO 2009/129546 A1 | 10/2009 |
| WO | WO 2009/129548 A1 | 10/2009 |
| WO | WO 2009/146216 A2 | 12/2009 |
| WO | WO 2009/146218 A2 | 12/2009 |
| WO | WO 2009/151910 A2 | 12/2009 |
| WO | WO 2010/008744 A2 | 1/2010 |
| WO | WO 2010/011782 A1 | 1/2010 |
| WO | WO 2010/045318 A2 | 4/2010 |
| WO | WO 2010/048477 A2 | 4/2010 |
| WO | WO 2010/054051 A1 | 5/2010 |
| WO | WO 2010/085845 A1 | 8/2010 |
| WO | WO 2010/091140 A1 | 8/2010 |
| WO | WO 2010/098627 A2 | 9/2010 |
| WO | WO 2010/104406 A1 | 9/2010 |
| WO | WO 2010/117633 A1 | 10/2010 |
| WO | WO 2010/120861 A1 | 10/2010 |
| WO | WO 2010/124009 A2 | 10/2010 |
| WO | WO 2010/129053 A2 | 11/2010 |
| WO | WO 2011/002857 A2 | 1/2011 |
| WO | WO 2011/008053 A2 | 1/2011 |
| WO | WO 2011/008054 A2 | 1/2011 |
| WO | WO 2011/025267 A2 | 3/2011 |
| WO | WO 2011/025269 A2 | 3/2011 |
| WO | WO 2011/025271 A2 | 3/2011 |
| WO | WO 2011/025720 A1 | 3/2011 |
| WO | WO 2011/038467 A1 | 4/2011 |
| WO | WO 2011/056741 A2 | 5/2011 |
| WO | WO 2011/060206 A2 | 5/2011 |
| WO | WO 2011/069962 A1 | 6/2011 |
| WO | WO 2011/070499 A1 | 6/2011 |

OTHER PUBLICATIONS

Cobleigh, et al., Multinational Study of the Efficacy and Safety of Humanized Anti-Her2 Monoclonal Antibody in Women Who Have HER2-Overexpressing Metastatic Breast Cancer That Has Progressed After Chemotherapy for Metastatic Disease, J. Clin. Oncol., Sep. 1999, 17(9):2639-2648.

Herceptin®—Product Literature, www.Genetech.com, Sep. 1998 revised (Nov. 2006), pp. 1-4.

Ikezoe, et al., The Anti-Tumor Effects of SU11248, a Class III Receptor Tyrosine Kinase Inhibitor, Against a Variety of Human Hematological Malignancies, Blood, Nov. 16, 2005, 106(11):784A—Abstract.

Ikezoe, et al., Effect of SU11248 on Gastrointestinal Stromal Tumor-T1 Cells: Enhancement of Growth Inhibition via Inhibition of 3-Kinase/Akt/Mammalian Target of Rapamycin Signaling, Cancer Science, Sep. 2006, 97(9):945-951.

Rabindran, et al., Antitumor Activity of HKI-272, an Orally Active, Irreversible Inhibitor of the HER-2 Tyrosine Kinase, Cancer Research, Jun. 1, 2004, 64:3958-3965.

Sakamoto, et al., SU-11248 SUGEN, Current Opinion in Investigational Drugs, Nov. 29, 2004, 5(12):1329-1339.

Merck Index, 13th Ed., No. 8202, Ed.: O'Neil, John Wiley & Sons (Oct. 15, 2001).

"Trastuzumab", Wikipedia, Aug. 14, 2009.

Correspondence from Peruvian associate regarding an Opposition filed against corresponding Peruvian Patent Application No. 001 342-2006/QIN dated 2007.

Correspondence from Israeli associate regarding a first Office Action issued in corresponding Israeli Patent Application No. 190805 dated 2010.

English translation of an Opposition filed against corresponding Ecuador Patent Application No. SP-08-8423 dated 2008.

Correspondence from Chilean associate regarding a first Office Action issued in corresponding Chilean Patent Application No. 2961-2006 dated 2009-2010.

Response filed by Applicant to Office Action dated Jul. 18, 2008 in corresponding European Patent Application No. 06836862.0.

"Vinorelbin." *Wikipedia: The Free Encyclopedia*. Wikimedia Foundation, Inc. Retrieved from the Internet on Jan. 28, 2013. URL:http://en.wikipedia.org/wiki/Vinorelbine.

Abbas et al., "A Drug Interaction Study to Evaluate the Effect of Ketoconazole on the Pharmacokinetics (PK) of Neratinib in Healthy Subjects," Clin. Pharmacol. Therapeutics 85:s44 (2009).

Abbas et al., "Evaluation of Neratinib (HKI-272) and Paclitaxel Pharmacokinetics (PK) in Asian and Caucasian Patients with Erbb2+ Breast Cancer: a Phase 1/2 Study of Neratinib in Combination with Paclitaxel," Ann. Oncol. 21:101 (2010).

Abbas et al., "Pharmacokinetics of Oral Neratinib During Co-Administration of Ketoconazole in Healthy Subjects," Br. J. Clin. Pharmacol. 71(4):522-527 (2011).

Abbas-Borhan et al., "A Clinical Study to Characterize the Occurrence of Mild-To-Moderate Diarrhea After Administration of Neratinib Either Once Daily or Twice Daily for 14 Days," EJC Suppl. 8:143 (2010).

Abbas-Borhan et al., "An Open-Label Study to Assess the Mass Balance and Metabolic Disposition of an Orally Administered Single Dose of 14C-Labeled Neratinib, an Irreversible pan-ErbB inhibitor, in Healthy Subjects," Drug Metab. Rev. 42:S1, 216 Abstr. P330 (2010).

Abramson and Arteaga, "New Strategies in HER2-Overexpressing Breast Cancer: Many Combinations of Targeted Drugs Available," Clin. Cancer Res. 17:952-958 (2011).

Adelaide et al., "Integrated Profiling of Basal and Luminal Breast Cancers," Cancer Res. 67(24):11565-11575 (2007).

Al-Dasooqi et al., "HER2 Targeted Therapies for Cancer and the Gastrointestinal Tract," Curr. Drug Targets 10(6):537-542 (2009).

Ali et al., "Mutational Spectra of PTEN/MMAC1 Gene: a Tumor Suppressor with Lipid Phosphatase Activity," J. Natl. Cancer Inst. 91(22):1922-1932 (1999).

Allegra et al., "American Society of Clinical Oncology Provisional Clinical Opinion: Testing for KRAS Gene Mutations in Patients With Metastatic Colorectal Carcinoma to Predict Response to Anti-Epidermal Growth Factor Receptor Monoclonal Antibody Therapy," J. Clin. Oncol. 27(12):2091-2096 (2009).

Al-Muhammed et al., "In-Vivo Studies on Dexamethasone Sodium Phosphate Liposomes," J. Microencapsul. 13(3):293-306 (1996).

Alvarez et al., "Emerging Targeted Therapies for Breast Cancer," J. Clin. Oncol. 28(20):3366-3379 (2010).

(56) References Cited

OTHER PUBLICATIONS

Álvarez, "Present and Future Evolution of Advanced Breast Cancer Therapy," Breast Cancer Res. 12(Suppl 2):S1 (2010).
Amslinger, "The tunable functionality of alpha,beta-unsaturated carbonyl compounds enables their differential application in biological systems," ChemMedChem. 5(3):351-356 (2010).
Andre and Diniz, "Targeted regimes without cytotoxics—are they ready for prime time?" EJC Suppl. 7:49 Abst. 191 (2009).
Andre et al., "Everolimus for women with trastuzumab-resistant, HER2-positive, advanced breast cancer (BOLERO-3): a randomised, double-blind, placebo-controlled phase 3 trial," Lancet Oncol. 15(6):580-591 (2014) (Epub Apr. 14, 2014).
Anonymous, "Trastuzumab", Wikipedia, Retrieved from the Internet on Nov. 21, 2014. URL:http://en.wikipedia.org/wiki/Trastuzumab?oldid=634842165.
Anonymous: "Meeting Archives of Chemotherapy Foundation Symposium XXIV, Nov. 7-10, 2007", The Chemotherapy Foundation, Nov. 8, 2007, Retrieved from the Internet on Jan. 13, 2010: URL:http://www.chemotherapyfoundationsymposium.org/meeting_archives/meetingarchives_tcf2007_main.html.
Anonymous: "Anticancer Agent—neratinib", Manufacturing Chemist, Dec. 2010/Jan. 2011, p. 27.
Arteaga, "ErbB-targeted therapeutic approaches in human cancer," Exp. Cell. Res. 284(1):122-130 (2003).
Awada and Piccart-Gebhart, "Management of HER-2/Neu-Positive Metastatic Breast Cancer," Eur. J. Cancer (Suppl. 6):2-9 (2008).
Awada et al., "Safety and Efficacy of Neratinib (HKI-272) in Combination with Vinorelbine in ErbB2+ Metastatic Breast Cancer," Cancer Res. 69:24(Suppl 3) Abstr. 5095 (2009).
Awada et al., "Safety and Efficacy of Neratinib (HKI-272) in Combination with Vinorelbine in ErbB2+ Metastatic Breast Cancer (MBC)," Ann. Oncol. 21(Suppl. 4):iv62-iv63 Abstr. 145P (2010).
Awada et al., "Safety and efficacy of neratinib (HKI-272) plus vinorelbine in the treatment of patients with ErbB2-positive metastatic breast cancer pretreated with anti-HER2 therapy," Ann. Oncol. 24(1):109-116 (2013) (Epub Sep. 11, 2012).
Azria et al., "[Radiotherapy and inhibitors of epidermal growth factor receptor: preclinical findings and preliminary clinical trials]," Bull Cancer. 90 Spec No:S202-S212 (2003). (Abstract only).
Badache and Goncalves, "The ErbB2 signaling network as a target for breast cancer therapy," J. Mammary Gland Biol. Neoplasia 11(1):13-25 (2006).
Barton et al., "Predictive molecular markers of response to epidermal growth factor receptor(EGFR) family-targeted therapies," Curr. Cancer Drug Targets 10(8):799-812 (2010).
Baselga and Swain, "Novel anticancer targets: revisiting ERBB2 and discovering ERBB3," Nat. Rev. Cancer 9(7):463-475 (2009) (Epub Jun. 18, 2009).
Baselga et al., "Phase I safety, pharmacokinetic, and pharmacodynamic trial of ZD1839, a selective oral epidermal growth factor receptor tyrosine kinase inhibitor, in patients with five selected solid tumor types," J. Clin. Onc. 20(21):4292-4302 (2002).
Baselga, "Is there a role for the irreversible epidermal growth factor receptor inhibitor EKB-569 in the treatment of cancer? A mutation-driven question," J. Clin. Oncol. 24(15):2225-2226 (2006).
Baselga, "Novel agents in the era of targeted therapy: what have we learned and how has our practice changed?" Ann. Oncol. 19(Suppl 7):vii281-vii288 (2008).
Baselga, "Treatment of HER2-Overexpressing Breast Cancer," Ann. Oncol. (Suppl 7):vii36-vii40 (2010).
Bayes et al., "Gateways to clinical trials," Methods Find. Exp. Clin. Pharmacol. 28(9):657-678 (2006).
Bedard et al., "Beyond trastuzumab: overcoming resistance to targeted HER-2 therapy in breast cancer," Curr. Cancer Drug Targets 9(2):148-162 (2009).
Bedard et al., "Stemming resistance to HER-2 targeted therapy," J. Mammary Gland Biol. Neoplasia.14(1):55-66 (2009) (Epub Mar. 4, 2009).

Belani, "The role of irreversible EGFR inhibitors in the treatment of non-small cell lung cancer: overcoming resistance to reversible EGFR inhibitors," Cancer Invest. 28(4):413-423 (2010).
Bell and Haber, "A blood-based test for epidermal growth factor receptor mutations in lung cancer," . Clin. Cancer Res. 12(13):3875-3877 (2006).
Berns et al., "A functional genetic approach identifies the PI3K pathway as a major determinant of trastuzumab resistance in breast cancer," Cancer Cell 12(4):395-402 (2007).
Berz and Wanebo, "Targeting the growth factors and angiogenesis pathways: small molecules in solid tumors," J. Surg. Oncol. 103(6):574-586 (2011).
Besse et al., "Neratinib (HKI-272), an irreversible pan-ErbB receptor tyrosine kinase inhibitor: preliminary results of a phase 2 trial in patients with advanced non-small cell lung cancer," Eur. J. Cancer (Suppl.):23 Abstr. 203 (2008).
Besse et al., "Targeted therapies in lung cancer," Ann. Oncol. 18(Suppl. 9):ix135-ix142 (2007).
Bettendorf et al., "Chromosomal imbalances, loss of heterozygosity, and immunohistochemical expression of TP53, RB1, and PTEN in intraductal cancer, intraepithelial neoplasia, and invasive adenocarcinoma of the prostate," Genes Chromosomes Cancer 47(7):565-572 (2008).
Bischoff and Ignatov, "The Role of Targeted Agents in the Treatment of Metastatic Breast Cancer," Breast Care (Basel) 5(3):134-141 (2010) (Epub Jun. 16, 2010).
Blanco-Aparicio et al., "PTEN, More Than the AKT Pathway," Carcinogenesis 28(7):1379-1386 (2007) (Epub Mar. 6, 2007).
Blanke, "Gefitinib in colorectal cancer: if wishes were horses," J. Clin. Oncol. 23(24):5446-5449 (2005).
Blencke et al., "Mutation of threonine 766 in the epidermal growth factor receptor reveals a hotspot for resistance formation against selective tyrosine kinase inhibitors," J. Biol. Chem. 278(17):15435-15440 (2003) (Epub Feb. 19, 2003).
Board et al., "Multiplexed assays for detection of mutations in PIK3CA," Clin. Chem 54(4):757-760 (2008).
Bonanno et al., "Mechanisms of acquired resistance to epidermal growth factor receptor tyrosine kinase inhibitors and new therapeutic perspectives in non small cell lung cancer," Curr. Drug Targets 12(6):922-933 (2011).
Boschelli et al., "Bosutinib: a review of preclinical studies in chronic myelogenous leukaemia," Eur. J. Cancer. 46(10):1781-1789 (2010).
Boschelli, "4-Anilino-3-quinolinecarbonitriles: An Emerging Class of Kinase Inhibitors—An Update," Med. Chem Rev. Online 1:457-463 (2004).
Bose and Ozer, "Neratinib: an oral, irreversible dual EGFR/HER2 inhibitor for breast and non-small cell lung cancer," Expert Opin. Investig. Drugs 18(11):1735-1751 (2009).
Bose et al., "Allelic loss of chromosome 10q23 is associated with tumor progression in breast carcinomas," Oncogene 17(1):123-127 (1998).
Bose et al., "Reduced expression of PTEN correlates with breast cancer progression," Hum. Pathol. 33(4):405-409 (2002).
Boyce et al., "Requirement of pp60c-src expression for osteoclasts to form ruffled borders and resorb bone in mice," J. Clin. Invest. 90(4):1622-1627 (1992).
Boyd et al., "Lapatanib: Oncolytic Dual EFGR and erbB-2 Inhibitor," Drugs Future 30(12):1225-1239 (2005).
Brackstone et al., "Canadian initiatives for locally advanced breast cancer research and treatment: inaugural meeting of the Canadian Consortium for LABC," Curr. Oncol. 18(3):139-144 (2011).
Bridges, "Current Progress Towards the Development of Tyrosine Kinase Inhibitors as Anticancer Agents," Expert Opin. Emerg. Drugs. 3:279-292 (1998).
Brittain, Harry G. (Eds), "Polymorphism in Pharmaceutical Solids", Chapters 1 and 5, Marcel Dekker, Inc., New York (1999).
Brook et al., "Management of transitional cell carcinoma by targeting the epidermal growth factor receptor," Therapy 3(3):407-416 (2006).
Browne et al., "HER-2 Signaling and Inhibition in Breast Cancer," Curr. Cancer Drug Targets 9(3):419-438 (2009).

(56) References Cited

OTHER PUBLICATIONS

Broxterman and Georgopapadakou, "Anticancer therapeutics: a surge of new developments increasingly target tumor and stroma," Drug Resist. Updat. 10(4-5):182-193 (2007) (Epub Sep. 12, 2007).
Buerger et al., "Allelic length of a CA dinucleotide repeat in the egfr gene correlates with the frequency of amplifications of this sequence—first results of an inter-ethnic breast cancer study," J. Pathol. 203(1):545-550 (2004).
Bullard Dunn et al., "Evolving Therapies and FAK Inhibitors for the Treatment of Cancer," Anticancer Agents Med. Chem. 10(10):722-734 (2010).
Burstein et al., "Gastrointestinal and Cardiovascular Safety Profiles of Neratinib Monotherapy in Patients with Advanced Erbb2-Positive Breast Cancer," Cancer Res. 69:Abst 5096 (2009).
Burstein et al., "HKI-272, an irreversible pan ErbB receptor tyrosine kinase inhibitor: preliminary phase 2 results in patients with advanced breast cancer," Breast Cancer Res. Treat. 106(Suppl. 1):S268 Abstr. 6061 (2007).
Burstein et al., "Neratinib (HKI-272), an irreversible pan ErbB receptor tyrosine kinase inhibitor: phase 2 results in patients with advanced HER2+ breast cancer," Cancer Res. 69(2 Suppl.) Abstr. 37 (2008).
Burstein et al., "Neratinib, an irreversible ErbB receptor tyrosine kinase inhibitor, in patients with advanced ErbB2-positive breast cancer," J. Clin. Oncol. 28(8):1301-1307 (2010).
Burstein, "The Distinctive Nature of HER2-Positive Breast Cancers," N. Engl. J. Med. 353(16):1652-1654 (2005).
Byrn et al., "Pharmaceutical solids: a strategic approach to regulatory considerations," Pharm. Res. 12(7):945-954 (1995).
Callahan and Hurwitz, "Human epidermal growth factor receptor-2-positive breast cancer: Current management of early, advanced, and recurrent disease," Curr. Opin. Obstet. Gynecol. 23(1):37-43 (2011).
Camp et al., "Molecular mechanisms of resistance to therapies targeting the epidermal growth factor receptor," Clin. Cancer Res. 11(1):397-405 (2005).
Campas et al., "BIBW-2992. Dual EGFR/HER2 Inhibitor Oncolytic;Tovok™," Drugs Future 33(8):649-654 (2008).
Campbel et al., "Gefitinib for the Treatment of Non-Small-Cell Lung Cancer," Expert Opin. Pharmacother. 11(8):1343-1357 (2010).
Cao et al., "Epidermal Growth Factor Receptor as a Target for Anti-Cancer Agent Design," Anticancer Agents Med. Chem. 10(6):491-503 (2010).
Cappuzzo et al., "Gefitinib in pretreated non-small-cell lung cancer (NSCLC): analysis of efficacy and correlation with HER2 and epidermal growth factor receptor expression in locally advanced or metastatic NSCLC," J. Clin. Oncol. 21(14):2658-2663 (2003).
Cappuzzo et al., "Surrogate predictive biomarkers for response to anti-EGFR agents: state of the art and challenges," Int. J. Biol. Markers 22(1 Suppl 4):S10-23 (2007).
Cardoso et al., "Locally Recurrent or Metastatic Breast Cancer: ESMO Clinical Practice Guidelines for Diagnosis, Treatment and Follow-Up," Ann. Oncol. 21(5):v15-v19 (2010).
Carney et al., "HER-2/neu diagnostics in breast cancer," Breast Cancer Res. 9(3):207 (2007).
Carter et al., "Small-Molecule Inhibitors of the Human Epidermal Receptor Family," Expert Opin. Investig. Drugs 18(12):1829-1842 (2009).
Cascone et al., "Epidermal Growth Factor Receptor Inhibitors in Non-Small-Cell Lung Cancer," Expert Opin. Drug Discov. 2(3):335-348 (2007).
Centre de Lutte Contre le Cancer Georges-Francois Leclerc (Fumoleau P. Study chair): "Lapatinib and Vinorelbine in Treating Women With HER2-Overexpressing Locally Advanced or Metastatic Breast Cancer" Clinical Trials Aug. 6, 2007 Retrieved from the Internet: URL:http://clinicaltrials.gov/ct2/show/NCT00513058?term=lapatinib+and+vinorelbine&rank=1 [retrieved on Jan. 13, 2010].
Chan and Giaccia, "Harnessing Synthetic Lethal Interactions in Anticancer Drug Discovery," Nat. Rev. Drug Discov. 10(5):351-364 (2011).

Chan, "A review of the use of trastuzumab (Herceptin®) plus vinorelbine in metastatic breast cancer," Ann. Oncol.18(7):1152-1158 (2007) (Epub Jan. 29, 2007) Review.
Chandrasekaran et al., "Reversible Covalent Binding of Neratinib to Human Serum Albumin in Vitro," Drug Metab. Lett. 4(4):220-227 (2010).
Chen et al., "Epidermal growth factor receptor inhibitors: current status and future directions," Curr. Probl. Cancer 33(4):245-294 (2009).
Chenoweth, "Can single-patient investigational new drug studies hurry slow trains to the fast track?" Drug Discov. Today 11(5-6):185-186 (2006).
Cheung and Paterson, "American Chemical Society—226th National Meeting. Pain and Oncology," Idrugs 6(10):935-936 (2003).
Chew, H. K. et al., EGFR Inhibition with Lapatinib in Combination with Vinorelbine: A Phase I Study, Chemotherapy Foundation Symposium Xxv, Chemotherapy Foundation, 2007, [Retrieved on Aug. 30, H-25 (2013)], obtained from the Internet, URL, http://chemotherapyfoundationsymposium.org/CMS/2007-archives-main.
Chew, Helen K., MD (University of California, Davis): "Lapatinib and Vinorelbine in Treating Patients With Advanced Solid Tumors" ClinicalTrials, Oct. 18, 2006, Retrieved from the Internet: URL:http//clinicaltrials.gov/ct2/show/NCT00389922?term=lapatinib+and+vinorelnine&rank=2 [retrieved on Jan. 13, 2010].
Chien and Rugo, "The Cardiac Safety of Trastuzumab in the Treatment of Breast Cancer," Expert Opin. Drug Saf. 9(2):335-346 (2010).
Chirieac and Dacic, "Targeted Therapies in Lung Cancer," Surg. Pathol. Clin. 3(1):71-82 (2010).
Chmielecki et al. Selection for the EGFR T790M gatekeeper resistance mutation may vary among different small molecule EGFR TKIs [abstract]. In: Proceedings of the 101st Annual Meeting of the American Association for Cancer Research; Apr. 17-21, 2010; Washington, DC. Philadelphia (PA): AACR; Cancer Res 2010;70(8 Suppl):Abstract nr 1774.
Cho et al., "Structure of the extracellular region of HER2 alone and in complex with the Herceptin Fab," Nature 421(6924):756-760 (2003).
Chonn et al., "Recent Advances in Liposomal Drug-Delivery Systems," Curr. Opin. Biotechnol. 6(6):698-708 (1995).
Choong et al., "Gefitinib response of erlotinib-refractory lung cancer involving meninges—role of EGFR mutation," Nat. Clin. Pract. Oncol. 3(1):50-57 (2006).
Chow et al., "Safety and efficacy of neratinib (HKI-272) in combination with paclitaxel in ErbB2+ metastatic breast cancer," Cancer Res. (Meeting Abstracts) 69:S5081 (2009).
Chow et al., "Safety and efficacy of neratinib (HKI-272) in combination with paclitaxel in patients with solid tumors," J. Clin. Oncol. (Meeting Abstracts) 27(155):3557 (2009).
Chow et al., "Safety and efficacy of neratinib (HKI-272) in combination with paclitaxel in ERBB2+ metastatic breast cancer (MBC)," Ann. Oncol. 21(Suppl 4):iv62 Abstr. 144P (2010).
Cicenas, "The Potential Role of the EGFR/ERBB2 Heterodimer in Breast Cancer," Expert Opin. Ther. Patents 17(6):607-616 (2007).
Clouser et al., "Biomarker Targets and Novel Therapeutics," Cancer Treat. Res. 149:85-105 (2009).
Cohen et al., "United States Food and Drug Administration Drug Approval summary: Gefitinib (ZD1839; Iressa) tablets," Clin. Cancer Res. 10(4):1212-1218 (2004).
Coldren et al., "Baseline gene expression predicts sensitivity to gefitinib in non-small cell lung cancer cell lines," Mol. Cancer Res. 4(8):521-528 (2006).
Collins et al., "Lapatinib: a competitor or companion to trastuzumab?" Cancer Treat. Rev. 35(7):574-581 (2009).
Colombo et al., "HER2 targeting as a two-sided strategy for breast cancer diagnosis and treatment: Outlook and recent implications in nanomedical approaches," Pharmacol. Res. 62(2):150-165 (2010) (Epub Feb. 1, 2010).
Cooper and Cohen, "Mechanisms of resistance to EGFR inhibitors in head and neck cancer," Head Neck 31(8):1086-1094 (2009).

(56) References Cited

OTHER PUBLICATIONS

Cortes-Funes et al., "Neratinib, an Irreversible Pan Erb Receptor Tyrosine Kinase Inhibitor Active for Advanced HER2+ Breast Cancer," Breast Cancer Res. 11 Suppl 1:S19 (2009).

Coughlin et al., "Approaches and limitations of phosphatidylinositol-3-kinase pathway activation status as a predictive biomarker in the clinical development of targeted therapy," Breast Cancer Res. Treat. 124(1):1-11 (2010) (Epub Aug. 28, 2010).

Cox, "Regression Models and Life Tables (With Discussion)," Journal of the Royal Statistical Society. Series B (Methodological), vol. 34, No. 2. (1972), pp. 187-220.

Da Cunha Santos et al., "EGFR Mutations and Lung Cancer," Ann. Rev. Pathol. 6:49-69 (2011).

Damia and D'Incalci, "Contemporary pre-clinical development of anticancer agents—what are the optimal preclinical models?" Eur. J. Cancer 45(16):2768-2781 (2009) (Epub Sep. 15, 2009).

Dancey, "Epidermal growth factor receptor inhibitors in non-small cell lung cancer," Drugs 67(8):1125-1138 (2007).

Dang et al.,"The safety of dose-dense doxorubicin and cyclophosphamide followed by paclitaxel with trastuzumab in HER-2/neu overexpressed/amplified breast cancer," J. Clin. Oncol. 26(8):1216-1222 (2008).

Daniele and Sapino, "Anti-HER2 treatment and breast cancer: state of the art, recent patents, and new strategies," Recent Pat. Anticancer Drug Discov. 4(1):9-18 (2009).

Davidian, M. (2006) Introduction to statistical population modeling and analysis for pharmacokinetic data. Invited white paper for the International Workshop on Uncertainty and Variability in Physiologically Based Pharmacokinetic (PBPK) Models. Retrieved from the Internet: URL:http://www.epa.gov/ncct/uvpkm/files/Calibration_PreMeeting_Draft.pdf (89 pages) [Retrieved on Jan. 29, 2014].

Davidson, "HER2-Targeted Therapies: How Far We've Come-And Where We're Headed," Oncology . (Williston Park) 25(5):425-426 (2011).

Davoli et al., "Progression and Treatment of HER2-Positive Breast Cancer," Cancer Chemother. Pharmacol. 65(4):611-623 (2010) (Epub Dec. 20, 2009).

De Bono and Rowinsky, "The ErbB receptor family: a therapeutic target for cancer," Trends Mol. Med. 8(4 Suppl):S19-S26 (2002).

De Luca and Normanno, "Predictive biomarkers to tyrosine kinase inhibitors for the epidermal growth factor receptor in non-small-cell lung cancer," Curr. Drug Targets 11(7):851-864 (2010).

De Maio et al., "Vinorelbine plus 3-weekly trastuzumab in metastatic breast cancer: a single-centre phase 2 trial," BMC Cancer. 7:50 (2007).

De Seranno and Meuwissen, "Progress and Applications of Mouse Models for Human Lung Cancer," Eur. Respir. J. 5(2):426-443 (2010).

Dempke and Heinemann, "Resistance to EGF-R (erbB-1) and VEGF-R modulating agents," Eur. J. Cancer 45(7):1117-1128 (2009) (Epub Jan. 3, 2009).

Depowski et al., "Loss of expression of the PTEN gene protein product is associated with poor outcome in breast cancer," Mod. Pathol. 14(7):672-676 (2001).

Di Cosimo and Baselga, "Management of breast cancer with targeted agents: importance of heterogeneity. [corrected]." Nat. Rev. Clin. Oncol. 7(3):139-147 (2010) (Epub Feb. 2, 2010).

Di Cosimo and Baselga, "Targeted Therapies in Breast Cancer: Where Are We Now?" Eur. J. Cancer 44(18):2781-2790 (2008) (Epub Nov. 14. 2008).

Di Maio et al., "New drugs in advanced non-small-cell lung cancer: searching for the correct clinical development," Expert Opin. Investig. Drugs 19(12):1503-1514 (2010) (Epub Nov. 4, 2010).

Dickler, "Updates on Therapeutic Approaches in HER2-Positive Disease," Clin. Adv. Hematol. Oncol. 8(2):105-107 (2010).

Dinh et al., "Trastuzumab for early breast cancer: current status and future directions," Clin. Adv. Hematol. Oncol. 5(9):707-717 (2007).

Dirix et al., "Neratinib Monotherapy in Patients with Advanced ERBB2-Positive Breast Cancer: Gastrointestinal and Cardiovascular Safety Profiles," Ann. Oncol. 21(Suppl 4):iv61-iv62 Abstr. 141P (2010).

Discafani et al., "Irreversible inhibition of epidermal growth factor receptor tyrosine kinase with in vivo activity by N-[4-[(3-bromophenyl)amino]-6-quinazolinyl]-2-butynamide (CL-387,785)," Biochem. Pharmacol. 57(8):917-925 (1999).

Doebele et al., "New strategies to overcome of reversible EGFR tyrosine kinase inhibitor limitations therapy in non-small cell lung cancer," Lung Cancer 69(1):1-12 (2010) (Epub Jan. 25, 2010).

Dorland's Illustrated Medical Dictionary. 31st ed. Philadelphia: Saunders Elsevier; c2007. Carcinoma; pp. 295-297.

Dowsett and Dunbier, "Emerging Biomarkers and New Understanding of Traditional Markers in Personalized Therapy for Breast Cancer," Clin. Cancer Res. 14(24):8019-8026 (2008).

Druker et al., "Efficacy and Safety of a Specific Inhibitor of the BCR-ABL Tyrosine Kinase in Chronic Myeloid Leukemia," N. Engl. J. Med. 344(14):1031-1037 (2001).

Eck and Yun, "Structural and Mechanistic Underpinnings of the Differential Drug Sensitivity of EGFR Mutations in Non-Small Cell Lung Cancer," Biochim. Biophys. Acta 1804(3):559-566 (2010).

Egloff and Grandis, "Targeting epidermal growth factor receptor and SRC pathways in head and neck cancer," Semin. Oncol. 35(3):286-297 (2008).

Eichhorn et al., "Phosphatidylinositol 3-kinase hyperactivation results in lapatinib resistance that is reversed by the mTOR/phosphatidylinositol 3-kinase inhibitor NVP-BEZ235," Cancer Res. 68(22):9221-9230 (2008).

Einhorn et al., "Summary Report 7th Annual Targeted Therapies of the Treatment of Lung Cancer," J. Thorac. Oncol. 3(5):545-555 (2008).

Einhorn, "Perspective on the Development of New Agents in Thoracic Cancers," Lung Cancer 50 Suppl 1:S27-S28 (2005).

Ellis and Crowder, "PIKing" the winner for phosphatidylinositol 3-kinase inhibitors in ErbB2-positive breast cancer: let's not "PTENed" it's easy! Clin. Cancer Res. 13(19):5661-5662 (2007).

Engelman and Settleman, "Acquired Resistance to Tyrosine Kinase Inhibitors During Cancer Therapy," Curr. Opin. Genet. Dev. 18(1):73-79 (2008) (Epub Mar. 5, 2008).

Engelman, "Targeting PI3K Signalling in Cancer: Opportunities, Challenges and Limitations," Nat. Rev. Cancer 9(8):550-562 (2009).

Engleman and Jänne, "Mechanisms of acquired resistance to epidermal growth factor receptor tyrosine kinase inhibitors in non-small cell lung cancer," Clin. Cancer Res. 14(10):2895-2899 (2008).

Ercan et al., "Amplification of EGFR T790M causes resistance to an irreversible EGFR inhibitor," Oncogene. 29(16):2346-2356 (2010) (Epub Feb. 1, 2010).

Esteva et al., "Molecular predictors of response to trastuzumab and lapatinib in breast cancer," Nat. Rev. Clin. Oncol. 7(2):98-107 (2010) (Epub Dec. 22, 2009).

Ettinger et al., "Antiemesis," J. Natl. Compr. Canc. Netw. 10(4):456-485 (2012).

Eyles et al., "Oral delivery and fate of poly(lactic acid) microsphere-encapsulated interferon in rats," J. Pharm. Pharmacol. 49(7):669-674 (1997).

Farley and Birrer, "Novel Therapeutic Targets," Cancer Treat. Res.149:63-84 (2009).

Felip et al., "Emerging Drugs for Non-Small-Cell Lung Cancer," Expert Opin. Emerg. Drugs 12(3):449-460 (2007).

Ferron et al., "Oral bioavailability of pantoprazole suspended in sodium bicarbonate solution," Am. J. Health Syst. Pharm. 60(13):1324-1329 (2003).

Ferté et al., "Molecular circuits of solid tumors: prognostic and predictive tools for bedside use," Nat. Rev. Clin. Oncol. 7(7):367-380 (2010) (Epub Jun. 15, 2010).

Fitch et al., "Genetics of dark skin in mice," Genes Dev. 17(2):214-228 (2003).

Fleming et al., "Nitrile-containing pharmaceuticals: efficacious roles of the nitrile pharmacophore," J. Med. Chem. 53(22)7902-7917 (2010) (Epub Aug. 30, 2010).

(56) References Cited

OTHER PUBLICATIONS

Fleming et al., "Phase II trial of temsirolimus in patients with metastatic breast cancer," Breast Cancer Res. Treat. 136(2):355-363 (2012) (Epub Jan. 13, 2012).
Folkman, "Angiogenesis in cancer, vascular, rheumatoid and other disease," Nat. Med. 1(1):27-31 (1995).
Frederick et al., "Epithelial to mesenchymal transition predicts gefitinib resistance in cell lines of head and neck squamous cell carcinoma and non-small cell lung carcinoma," Mol. Cancer Ther. 6(6):1683-1691 (2007) (Epub May 31, 2007).
Früh, "The search for improved systemic therapy of non-small cell lung cancer—what are today's options?" Lung Cancer 72(3):265-270 (2011) (Epub Apr. 14, 2011).
Fry, "Inhibition of the epidermal growth factor receptor family of tyrosine kinases as an approach to cancer chemotherapy: progression from reversible to irreversible inhibitors," Pharmacol. Ther. 82(2-3):207-218 (1999).
Fukuoka et al., "Multi-institutional randomized phase II trial of gefitinib for previously treated patients with advanced non-small-cell lung cancer (The IDEAL 1 Trial) [corrected]," J. Clin. Oncol. 21(12):2237-2246 (2003) (Epub May 14, 2003).
Gadji et al., "EGF receptor inhibitors in the treatment of glioblastoma multiform: old clinical allies and newly emerging therapeutic concepts," Eur. J. Pharmacol. 625(1-3):23-30 (2009) (Epub Oct. 18, 2009).
Gajria and Chandarlapaty, "HER2-amplified breast cancer: mechanisms of trastuzumab resistance and novel targeted therapies," Expert Rev. Anticancer Ther. 11(2):263-275 (2011).
Gajria et al., "Tolerability and Efficacy of Targeting Both mTOR and HER2 Signaling in Trastuzumab-Refractory HER2+ Metastatic Breast Cancer," San Antonio Breast cancer Symposium. Abstract P5-18-04 (2010).
Gao et al., "Controlled Release of a Contraceptive Steroid From Biodegradable and Injectable Gel Formulations: in Vitro Evaluation," Pharm. Res. 12:857-863 (1995).
Garcia et al., "Promoter Methylation of the PTEN Gene Is a Common Molecular Change in Breast Cancer," Genes Chromosomes Cancer 41(2):117-127 (2004).
Garrett and Arteaga, "Resistance to HER2-directed antibodies and tyrosine kinase inhibitors: mechanisms and clinical implications," Cancer Biol. Ther. 11(9):793-800 (2011) (Epub May 1, 2011).
Gatzemeier, "Second-Generation EGFR Inhibitors and Combinations," J. Thorac Oncol. 4(9): S121 (2009).
Gazdar, "Activating and Resistance Mutations of EGFR in Non-Small-Cell Lung Cancer: Role in Clinical Response to EGFR Tyrosine Kinase Inhibitors," Oncogene 28:S24-S31 (2009).
Gennaro (Ed.), Remington's Pharmaceutical Sciences, 17th Edition, Alfonso R. Gennaro, Mack.. Publishing Company, Easton, PA (1985).
Geuna et al., "Hitting multiple targets in HER2-positive breast cancer: proof of principle or therapeutic opportunity?" Expert Opin. Pharmacother. 12(4):549-565 (2011) (Epub Jan. 6, 2011).
Geyer et al., "Lapatinib plus capecitabine for HER2-positive advanced breast cancer," N. Engl. J. Med. 355(26):2733-2743 (2006).
Ghayad and Cohen, "Inhibitors of the PI3K/Akt/mTOR pathway: new hope for breast cancer patients," Recent Pat. Anticancer Drug Discov. 5(1):29-57 (2010).
Giaccone et al., "Gefitinib in combination with gemcitabine and cisplatin in advanced non-small-cell lung cancer: a phase III trial—INTACT 1," J. Clin. Oncol. 22(5):777-784 (2004).
Giamas et al., "Kinases as Targets in the Treatment of Solid Tumors," Cell. Signal. 22(7):984-1002 (2010) (Epub Jan. 21, 2010).
Glaxosmithkline, TYKERB Prescription Label, 2010, pp. 1-25.
Glück, "Chemotherapy Regimens in Metastatic Breast Cancer," Clin. Adv. Hematol. Oncol. 9(1)47-48 (2011).
Godin-Heymann et al., "Oncogenic activity of epidermal growth factor receptor kinase mutant alleles is enhanced by the T790M drug resistance mutation," Cancer Res. 67(15):7319-7326 (2007).

Godin-Heymann et al., "The T790M "gatekeeper" mutation in EGFR mediates resistance to low concentrations of an irreversible EGFR inhibitor," Mol. Cancer Ther. 7(4):874-879 (2008).
Good, "A Comparison of Contact Angle Interpretations," J. Colloid Interface Sci. 44(1):63-71 (1973).
Govindan, "A review of epidermal growth factor receptor/HER2 inhibitors in the treatment of patients with non-small-cell lung cancer," Clin. Lung Cancer 11(1):8-12 (2010).
Greenberger et al., "EKB-569: a New Irreversible Inhibitor of Epidermal Growth Factor Receptor Tyrosine Kinase for the Treatment of Cancer," Clin. Cancer Res. 6(Suppl):4544s Abstr. 388 (2000).
Greulich et al., "Oncogenic Transformation by Inhibitor-Sensitive and -Resistant EGFR Mutants," PLOS Medicine 2(11) E313:1167-1176 (2005).
Gridelli et al., "Erlotinib in the Treatment of Non-small Cell Lung Cancer: Current Status and Future Developments," Anticancer Res. 30:1301-1310 (2010).
Grimm et al., "Diagnostic and Therapeutic Use of Membrane Proteins in Cancer Cells," Curr. Med. Chem. 18(2):176-190 (2011).
Guarneri et al., "Anti-HER2 neoadjuvant and adjuvant therapies in HER2 positive breast cancer," Cancer Treat. Rev. 36 Suppl 3:S62-S66 (2010).
Guertin et al., "Ablation in mice of the mTORC components raptor, rictor, or mLST8 reveals that mTORC2 is required for signaling to Akt-FOXO and PKCalpha, but not S6K1," Dev. Cell. 11(6):859871 (2006).
Gullick et al., "Expression of epidermal growth factor receptors on human cervical, ovarian, and vulval carcinomas," Cancer Res. 46(1):285-292 (1986).
Hager et al., "PTEN expression in renal cell carcinoma and oncocytoma and prognosis," Pathology 39(5):482-485 (2007) (Abstract Only).
Hammerman et al., "Resistance to Epidermal Growth Factor Receptor Tyrosine Kinase Inhibitors in Non-Small Cell Lung Cancer," Clin. Cancer Res. 15(24):7502-7509 (2009).
Harris et al., "c-erbB-2 in serum of patients with breast cancer," Int. J. Biol. Markers 14(1):8-15 (1999).
Hasselblatt, "Ependymal Tumors," Recent Results Cancer Res. 171:51-66 (2009).
Hawkins and Grunberg, "Chemotherapy-Induced Nausea and Vomiting: Challenges and Opportunities for Improved Patient Outcomes," Clin. J. Oncol. Nurs. 13(1):54-64 (2009).
Hegedus et al., "Interaction of ABC multidrug transporters with anticancer protein kinase inhibitors: substrates and/or inhibitors?" Curr. Cancer Drug Targets 9(3):252-272 (2009).
Heigener and Reck, "Mutations in the epidermal growth factor receptor gene in non-small-cell lung cancer: Impact on treatment beyond gefitinib and erlotinib," Adv. Ther. 28(2):126-133 (2011) (Epub Dec. 16, 2010).
Heigener, "Non-Small Cell Lung Cancer in Never-Smokers: a New Disease Entity?" Onkologie 34(4):202-207 (2011) (EpubMar. 18, 2011).
Heist et al., "A phase II study of oxaliplatin, pemetrexed, and bevacizumab in previously treated advanced non-small cell lung cancer," J. Thorac. Oncol. 3(10):1153-1158 (2008).
Herbst et al., "Gefitinib in Combination with Paclitaxel and Carboplatin in Advanced Non-Small-Cell Lung Cancer: a Phase III Trial-INTACT 2," J. Clin. Oncol. 22(5):785-794 (2004).
Herbst et al., "Selective oral epidermal growth factor receptor tyrosine kinase inhibitor ZD1839 is generally well-tolerated and has activity in non-small-cell lung cancer and other solid tumors: results of a phase I trial," J. Clin. Oncol. 20(18):3815-3825 (2002).
Heymach et al., "Epidermal growth factor receptor inhibitors in development for the treatment of non-small cell lung cancer," Clin. Cancer Res. 12(14 Pt 2):4441s-4445s (2006).
Higa et al., "Biological considerations and clinical applications of new HER2-targeted agents," Expert Rev. Anticancer Ther. 10(9):1497-1509 (2010).
Ho and Laskin, "EGFR-directed therapies to treat non-small-cell lung cancer," Expert Opin. Investig. Drugs 18(8):1133-1145 (2009).
Holbro and Hynes, "ErbB receptors: directing key signaling networks throughout life," Annu. Rev. Pharmacol. Toxicol. 44:195-217 (2004).

(56) References Cited

OTHER PUBLICATIONS

Holodov and Yakovlev, Clinical Pharmacokinetics, Moscow, Medicine, (1985), pp. 83-98, 134-138, 160, 378-380 (English translation not available).
Hookes and Lakeram, "American Chemical Society—235th National Meeting. Part 2: EGFR kinaseinhibitors and β3-lactamases under investigation by Wyeth" Idrugs 11(6):391-393 (2008).
Horn and Sandler, "Epidermal growth factor receptor inhibitors and antiangiogenic agents for the treatment of non-small cell lung cancer," Clin. Cancer Res. 15(16):5040-5048 (2009) (Epub Aug. 11, 2009).
Hou and Kumamoto, "Flavonoids as protein kinase inhibitors for cancer chemoprevention: direct binding and molecular modeling," Antioxid. Redox Signal. 13(5):691-719 (2010).
Huang et al., "Up-regulation of miR-21 by HER2/neu signaling promotes cell invasion," J. Biol. Chem. 284(27):18515-18524 (2009) (Epub May 6, 2009).
Hubalek et al., "Resistance to HER2-targeted therapy: mechanisms of trastuzumab resistance and possible strategies to overcome unresponsiveness to treatment," Wien. Med. Wochenschr. 160(1920):506-512 (2010) (Epub Oct. 26, 2010).
Huber et al., "Pharmacokinetics of pantoprazole in man," Int. J. Clin. Pharmacol. Ther. 34(5):185-194 (1996).
Hug et al., "A single-dose, crossover, placebo- and moxifloxacin-controlled study to assess the effects of neratinib (HKI-272) on cardiac repolarization in healthy adult subjects," Clin. Cancer Res. 16(15):4016-4023 (2010) (Epub Jul. 20, 2010).
Hung and Lau, "Basic Science of HER-2/neu: a review," Semin. Oncol. 26(4 Suppl 12):51-59 (1999).
Hungarian Intellectual Property Office Search Report for Hungarian Patent Application No. 201002712-6 (dated Aug. 4, 2011).
Hynes and Lane, "ERBB Receptors and Cancer: the Complexity of Targeted Inhibitors," Nat. Rev. Cancer 5(5):341-354 (2005).
ICH Expert Working Group: "Impurities in New Drug Substances Q3A (R2), International Conference on Harmonisation of Technical Requirements for Registration of Pharmaceuticals for Human Use" (Online) 2006.
Ikediobi, "Somatic Pharmacogenomics in Cancer," Pharmacogenomics J. 8(5):305-314 (2008) (Epub Aug. 5, 2008).
Ikezoe et al., "Effect of SU11248 on gastrointestinal stromal tumor-T1 cells: enhancement of growth inhibition via inhibition of 3-kinase/Akt/mammalian target of rapamycin signaling," Cancer Sci. 97(9):945-951 (2006).
Ilango et al., "Investigation of Colon Specificity of Novel Polysaccharide-Okra Mucilage-Film Coated with Enteric Materials," Int. J. Pharma. Bio. Sci. 3(2):52-62 (2012).
Iliadis et al., "APIS: a software for model identification, simulation and dosage regimen calculations in clinical and experimental pharmacokinetics," Computer Methods Programs Biomed. 38(4):227-239 (1992).
International Perliminary Report on Patentability Chapter 1 for International Application No. PCT/US2009/047643 dated Dec. 18, 2010.
International Search Report for International Application No. PCT/US2008/080130, dated Apr. 5, 2009.
International Search Report for International Patent Application No. PCT/US2009/047643, dated Jan. 28, 2010.
Isakoff and Baselga, "Trastuzumab-DM1: building a chemotherapy-free road in the treatment of human epidermal growth factor receptor 2-positive breast cancer," J. Clin. Oncol. 29(4):351-354 (2011) (Epub Dec. 20, 2010).
Ito et al., "A Phase 1 Study of Neratinib (HKI-272) in Combination with Paclitaxel in Japanese . Patients with Solid Tumors," Ann. Oncol. 21 (Suppl 8):viii103 Abstr. 298P (2010).
Ito et al., "Tolerability and safety of oral neratinib (HKI-272) in Japanese patients with advanced solid tumors," J. Clin. Oncol. 27:(suppl; abstr. e14505) (2009).
Jackisch, "Challenges in the treatment of ErbB2 (HER2)-positive breast cancer," EJC Suppl. 6(5):7-14 (2008).
Jahanzeb et al., "Phase II trial of weekly vinorelbine and trastuzumab as first-line therapy in patients with HER2+ metastatic breast cancer," Oncologist 7(5):410-417 (2002).
Jallal et al., "A Src/Abl kinase inhibitor, SKI-606, blocks breast cancer invasion, growth, and metastasis in vitro and in vivo," Cancer Res. 67(4):1580-1588 (2007).
Janczuk and Bialopiotrowicz, "Surface Free-Energy Components of Liquids and Low Energy . Solids and Contact Angles," J. Colloid Interface Sci. 127(1):189-204 (1989).
Jänne et al., "Phase I dose-escalation study of the pan-HER inhibitor, PF299804, in patients with advanced malignant solid tumors," Clin. Cancer Res. 17(5):1131-1139 (2011) (Epub Jan. 10, 2011).
Jänne, "Challenges of detecting EGFR T790M in gefitinib/erlotinib-resistant tumours," Lung Cancer 60 Suppl 2:S3-S9 (2008).
Japanese Official Action for Corresponding Japanese Patent Application No. 2010-258729, dated Apr. 12, 2013.
Japanese Official Action dated Sep. 17, 2013, for Japanese Patent Application No. 2011-289220.
Jasper, "The Surface Tension of Pure Liquid Compounds," J. Phys. Chem. Ref. Data 1:841 (1972).
Jelliffe et al., "Adaptive control of drug dosage regimens: basic foundations, relevant issues, and . clinical examples," Int. J. Biomed. Comput. 36(1-2):1-23 (1994).
Ji et al., "Epidermal growth factor receptor variant III mutations in lung tumorigenesis and sensitivity to tyrosine kinase inhibitors," Proc. Natl. Acad. Sci. U.S.A. 103(20):7817-7822 (2006) (Epub May 3, 2006).
Ji et al., "The impact of human EGFR kinase domain mutations on lung tumorigenesis and in vivo sensitivity to EGFR-targeted therapies," Cancer Cell. 9(6):485-495 (2006) (Epub May 25, 2006).
Jimeno and Hidalgo, "Pharmacogenomics of epidermal growth factor receptor (EGFR) tyrosine kinaseinhibitors," Biochim. Biophys. Acta 1766(2):217-229 (2006) (Epub Sep. 12, 2006).
Johnson et al., "Cisplatin and Its Analogues," Cancer Principles & Practice of Oncology, 6th Edition, Ed. Devita, V.T., Hellman, S., Rosenberg, S.A, Lippincott Williams & Wilkins Philadelphia, 2001, p.
Johnson et al., "Impact of EGFR mutations on treatment of non-small cell lung cancer," Cancer Chemother. Pharmacol. 58(Suppl1):s5-s9 (2006).
Johnson et al., "Strategies for discovering and derisking covalent, irreversible enzyme inhibitors," Future Med. Chem. 2(6):949-964 (2010).
Johnson, "Biomarkers of Lung Cancer Response to EGFR-TKI," EJC Suppl. 5(8):14-15 Abstr. S23 (2007).
Johnson, "Protein kinase inhibitors: contributions from structure to clinical compounds," Q. Rev. Biophys. 42(1):1-40 (2009) (Epub Mar. 19, 2009).
Jones and Buzdar, "Evolving Novel Anti-HER2 Strategies," Lancet Oncol. 10(12):1179-1187 (2009).
Jones, "Adaptive trials receive boost," Nat. Rev. Drug Discov. 9(5):345-348 (2010) (Epub Apr. 23, 2010).
Jones, "HER4 intracellular domain (4ICD) activity in the developing mammary gland and breast cancer," J. Mammary Gland Biol. Neoplasia 13(2):247-258 (2008) (Epub May 13, 2008).
Jorissen et al., "Epidermal growth factor receptor: mechanisms of activation and signalling," Exp. Cell. Res. 284(1):31-53 (2003).
Joshi and Kucherlapati, "Pharmacogenomics of lung cancer: with a view to address EGFR-targeted therapies," Pharmacogenomics 8(9):1211-1220 (2007).
Kamath and Buolamwini, "Targeting EGFR and HER-2 receptor tyrosine kinases for cancer drug discovery and development," Med. Res. Rev. 26(5):569-594 (2006).
Kane, "Cancer Therapies Targeted to the Epidermal Growth Factor Receptor and Its Family Members," Expert Opin. Ther. Pat. 16(2):147-164 (2006).
Kaplan and Meier, "Nonparametric Estimation From Incomplete Observations," J. Am. Stat. Assoc. 53:457-481 (1958).
Katakami et al., "LUX-Lung 4: a phase II trial of afatinib in patients with advanced non-small-cell lung cancer who progressed during prior treatment with erlotinib, gefitinib, or both," J. Clin. Oncol. 31(27):3335-3341 (2013) (Epub Jul. 1, 2013).

(56) References Cited

OTHER PUBLICATIONS

Katzel et al., "Recent advances of novel targeted therapy in non-small cell lung cancer," J Hematol. Oncool. 2:2 (2009).
Kennedy et al., "Novel Agents in the Management of Lung Cancer," Curr. Med. Chem. 17(35):4291-4325 (2010).
Kim et al., "Chasing targets for EGFR tyrosine kinase inhibitors in non-small-cell lung cancer: Asian perspectives," Expert Rev. Mol. Diagn.7(6):821-836 (2007).
Kim et al., "The role of HER-2 oncoprotein in drug-sensitivity in breast cancer (Review)," Oncol. Rep. 9(1):3-9 (2002).
Klein and Levitzki, "Targeting the EGFR and the PKB Pathway in Cancer," Curr. Opin. Cell. Biol. 21(2):185-193 (2009) (Epub Feb. 11, 2009).
Klüter et al., "Characterization of irreversible kinase inhibitors by directly detecting covalent bond formation: a tool for dissecting kinase drug resistance," ChemBioChem 11(18):2557-2566 (2010).
Kobayashi et al., "EGFR mutation and resistance of non-small-cell lung cancer to gefitinib," N. Engl. J. Med. 352(8):786-792 (2005).
Kotteas et al., "Targeted therapy for nonsmall cell lung cancer: focusing on angiogenesis, the epidermal growth factor receptor and multikinase inhibitors," Anticancer Drugs 21(2):151-168 (2010).
Kris et al., "Efficacy of gefitinib, an inhibitor of the epidermal growth factor receptor tyrosine kinase, in symptomatic patients with non-small cell lung cancer: a randomized trial," JAMA 290(16):2149-2158 (2003).
Krop, "Managing Trastuzumab-resistant Breast Cancer," Clin. Adv. Hematol. Oncol. 7(2):108-110 (2009).
Kuznar, "New Small Molecule Added to Trastuzumab Improves Survival in Metastatic Disease," Am. Health Drug Benefits 2(5):27 (2009).
Kwak et al., "Irreversible inhibitors of the EGF receptor may circumvent acquired resistance to gefitinib," Proc. Natl. Acad. Sci. U.S.A. 102(21):7665-7670 (2005) (Epub May 16, 2005).
La Motta et al., "Computational studies of epidermal growth factor receptor: docking reliability, three-dimensional quantitative structure-activity relationship analysis, and virtual screening studies," J. Med. Chem. 52(4):964-975 (2009).
Laack et al., "Lessons learnt from gefitinib and erlotinib: Key insights into small-molecule EGFR-targeted kinase inhibitors in non-small cell lung cancer," Lung Cancer 69(3):259-264 (2010) (Epub Jun. 19, 2010).
Lam and Mok, "Targeted Therapy: An Evolving World of Lung Cancer," Respirology 16(1):13-21 (2011) (Epub Aug. 16, 2010).
Langdon et al., "Pertuzumab—Humanized anti-HER2 monoclonal antibody HER dimerization inhibitor oncolytic," Drugs Future 33(2):123-130 (2008).
Langer and Soria, "The role of anti-epidermal growth factor receptor and anti-vascular endothelial growth factor therapies in the treatment of non-small-cell lung cancer," Clin. Lung Cancer 11(2):82-90 (2010).
Langlois et al., "Application of a modification of the Polonovski reaction to the synthesis of vinblastine-type alkaloids," J. Am. Chem. Soc. 98(22):7017-7024 (1976).
Lapatinib and Vinorelbine in Treating Patients with Advanced Solid Tumors, clinicaltrials.gov, [Online], U.S. National Institutes of Health, May 26, 2008, [Retrieved on Aug. 30, H-25 (2013)], obtained from the Internet, URL, http://clinicaltrials.gov/archive/NCT00389922/2008_05_26.
Lapatinib and Vinorelbine in Treating Women With HER2-Overexpressing Locally Advanced or Metastatic Breast Cancer, http://clinicaltrials.gov, [Online], U.S. National Institutes of Health, May 26, 2008, [Retrieved on Aug. 30, H-25 (2013)], obtained from the Internet, URL, http://clinicaltrials.gov/archive/NCT00513058/2008_05_26.
Lee et al., "Lung Cancer in Never Smokers: Change of a Mindset in the Molecular Era," Lung Cancer 72(1):9-15 (2011) (Epub Jan. 26, 2011).
Lee et al., "Phase II Study of Vinorelbine Plus Trastuzumab in HER2 Overexpressing Metastatic Breast Cancer Pretreated with Anthracyclines and Taxanes," J. Breast Cancer 14(2):140-146 (2011).

Leone and Dudek, "Enzyme replacement therapy for Gaucher's disease in patient treated for non-small cell lung cancer," Anticancer Res. 28(6B):3937-3939 (2008).
Levitzki and Mishani, "Tyrphostins and other tyrosine kinase inhibitors," Annu. Rev. Biochem. 75:93-109 (2006).
Li and Perez-Soler, "Skin toxicities associated with epidermal growth factor receptor inhibitors," Target. Oncol. 4(2):107-119 (2009) (Epub May 19, 2009).
Li and Sun, "PTEN/MMAC1/TEP1 suppresses the tumorigenicity and induces G1 cell cycle arrest in human glioblastoma cells," Proc. Natl. Acad. Sci. U.S.A. 95(26):15406-15411 (1998).
Li and Sun, "TEP1, encoded by a candidate tumor suppressor locus, is a novel protein tyrosine phosphatase regulated by transforming growth factor β," Cancer Res. 57(11):2124-2129 (1997).
Li et al., "BIBW2992, an irreversible EGFR/HER2 inhibitor highly effective in preclinical lung cancer models," Oncogene 27(34):4702-4711 (2008) (Epub Apr. 14, 2008).
Li et al., "Bronchial and peripheral murine lung carcinomas induced by T790M-L858R mutant EGFR respond to HKI-272 and rapamycin combination therapy," Cancer Cell 12(1):81-93 (2007).
Li et al., "PTEN, a putative protein tyrosine phosphatase gene mutated in human brain, breast, and prostate cancer," Science 275(5308):1943-1947 (1997).
Ligibel and Winer, "Trastuzumab/chemotherapy combinations in metastatic breast cancer," Semin. Oncol. 29(3 Suppl 11):38-43 (2002).
Limentani et al., "Safety and Efficacy of Neratinib (HKI-272) in Combination with Vinorelbine in Patients with Solid Tumors," J. Clin. Oncol. (Meeting Abstracts) 27(15S):e14554 (2009).
Lin and Winer, "Chemotherapy agents in human epidermal growth factor receptor 2-positive breast cancer: time to step out of the limelight," J. Clin. Oncol. 29(3):251-253 (2011) (Epub Dec. 13, 2010).
Lin and Yang, "Epidermal growth factor receptor tyrosine kinase inhibitors in elderly or poor performance status patients with advanced non-small cell lung cancer," Target. Oncol. 4(1):37-44 (2009) (Epub Jan. 20, 2009).
Linardou et al., "Somatic EGFR mutations and efficacy of tyrosine kinase inhibitors in NSCLC," Nat. Rev. Clin. Oncol. 6(6):352-366 (2009).
Little, "Molecular Tests, Targets and Therapies for Cancer," EPC (DIA 43rd Annual Meeting Edition) p. 98 (2007).
Liu et al., "Targeting epidermal growth factor receptor in lung cancer: Perspective from the Asia—Pacific region," Asia-Pac. J. Clin. Oncol. 2:22-31 (2006).
Locker et al., "ASCO 2006 update of recommendations for the use of tumor markers in gastrointestinal cancer," J. Clin. Oncol. 24(33):5313-5327 (2006) (Epub Oct. 23, 2006).
Loew et al., "The epidermal growth factor receptor as a therapeutic target in glioblastoma multiforme and other malignant neoplasms," Anticancer Agents Med. Chem. 9(6):703-715 (2009).
Loke, "Drug-drug interactions—bridging the gulf between the bench and the bedside?" Br. J. Clin. Pharmacol. 71(4):485-486 (2011).
LoPiccolo et al., "Targeting the PI3K/Akt/mTOR pathway: effective combinations and clinical considerations," Drug Resist. Updat. 11(1-2):32-50 (2008) (Epub Dec. 31, 2007).
Loriot et al., "Drug insight: gastrointestinal and hepatic adverse effects of molecular-targeted agents in cancer therapy," Nat. Clin. Pract. Oncol. 5(5):268-278 (2008) (Epub Mar. 18, 2008).
Loriot et al., "Pemetrexed-induced pneumonitis: a case report," Clin. Lung Cancer 10(5):364-366 (2009).
Lorus So and Eder, "Therapeutic potential of novel selective-spectrum kinase inhibitors in oncology," Expert Opin. Investig. Drugs 17(7):1013-1028 (2008).
Lou et al., "Progress in Target Therapy for Breast Cancer," J. Oncology 15(9):788-795 (2009). (English Abstract).
Lu and Ku, "Preformulation stability study of the EGFR inhibitor HKI-272 (Neratinib) and mechanism of degradation," Drug Dev. Ind. Pharm. 1-7 (2011).
Lu et al., "The PTEN/MMAC1/TEP tumor suppressor gene decreases cell growth and induces apoptosis and anoikis in breast cancer cells," Oncogene 18(50):7034-7045 (1999).

(56) References Cited

OTHER PUBLICATIONS

Luetteke et al., "The mouse waved-2 phenotype results from a point mutation in the EGF receptor tyrosine kinase," Genes Dev. 8(4):399-413 (1994).
Lynch et al., "Activating mutations in the epidermal growth factor receptor underlying responsiveness of non-small-cell lung cancer to gefitinib," N. Engl. J. Med. 350(21):2129-2139 (2004) (Epub Apr. 29, 2004).
Lynch et al., "Novel Agents in the Treatment of Lung Cancer: Fourth Cambridge Conference," Clin. Cancer Res. 13(15 Suppl.):4583s-4588s (2007).
Lynch et al., "Summary statement novel agents in the treatment of lung cancer: Fifth Cambridge Conference assessing opportunities for combination therapy," J. Thorac. Oncol. 3(6 Suppl 2):S107-S112 (2008).
Lynch, "Molecular Staging of NSCLC: 2006," EJC (Suppl 4):24-25 Abstr. S55 (2006).
Ma et al., "PIK3CA as an oncogene in cervical cancer," Oncogene 19(23):2739-2744 (2000).
Macrinici and Romond, "Clinical updates on EGFR/HER targeted agents in early-stage breast cancer," Clin. Breast Cancer 10 Suppl 1:E38-E46 (2010).
Maehama et al., "A sensitive assay for phosphoinositide phosphatases," Anal. Biochem. 279(2):248-250 (2000).
Maehama et al., "PTEN and myotubularin: novel phosphoinositide phosphatases," Annu. Rev. Biochem. 70:247-279 (2001).
Maehama, "PTEN: its deregulation and tumorigenesis," Biol. Pharm. Bull. 30(9):1624-1627 (2007).
Mallon et al., "Antitumor efficacy of PKI-587, a highly potent dual PI3K/mTOR kinase inhibitor," Clin. Cancer Res. 17(10):3193-3203 (2011) (Epub Feb. 15, 2011).
Man et al., "New and established targets for the treatment of breast cancer," Adv. Breast Cancer 7(3):10-13 (2010).
Mangeney et al., "5'-Nor anhydrovinblastine : Prototype of a new class of vinblastine derivatives," Tetrahedron 35(18):2175-2179 (1979).
Mantel and Haenszel, "Statistical aspects of the analysis of data from retrospective studies of disease," J. Natl. Cancer Inst. 22(4):719-748 (1959).
Martinez-Garcia et al., "Tyrosine Kinase Inhibitors in Breast Cancer: Present Status and Perspectives," Cancer Chemother. Rev. 186-194 (2010).
Mattsson and Clowes, "Current concepts in restenosis following balloon angioplasty," Trends Cardiovasc. Med. 5(5):200-204 (1995).
Mauriz and Gonzalez-Gallego, "Antiangiogenic drugs: current knowledge and new approaches to cancer therapy," J. Pharm. Sci. 97(10):4129-4154 (2008).
Mayer, "Treatment of HER2-positive metastatic breast cancer following initial progression," Clin. Breast Cancer 9 Suppl 2:S50-S57 (2009).
McDermott et al., "Acquired resistance of non-small cell lung cancer cells to MET kinase inhibition is mediated by a switch to epidermal growth factor receptor dependency," Cancer Res. 70(4):1625-1634 (2010) (Epub Feb. 2, 2010).
McDermott et al., "High-throughput lung cancer cell line screening for genotype-correlated sensitivity to an EGFR kinase inhibitor," Methods Enzymol. 438:331-341 (2008).
McDermott et al., "Identification of genotype-correlated sensitivity to selective kinase inhibitors by using high-throughput tumor cell line profiling," Proc. Natl. Acad. Sci. U.S.A. 104(50):19936-19941 (2007) (Epub Dec. 6, 2007).
Mehta and Osipo, "Trastuzumab resistance: role for Notch signaling," ScientificWorldJournal 9:1438-1448 (2009).
Mendelsohn and Baselga, "The EGF receptor family as targets for cancer therapy," Oncogene 19(56):6550-6565 (2000).
Mendoza, "Targeted therapies in the treatment of advanced non-small-cell lung cancer: update," Klin. Onkol. 22(4):131-138 (2009).
Meng et al., "MicroRNA-21 regulates expression of the PTEN tumor suppressor gene in human hepatocellular cancer," Gastroenterology 133(2):647-658 (2007) (Epub May 21, 2007).
Metro and Cappuzzo, "New targeted therapies for non-small-cell lung cancer," Therapy 6(3):335-350 (2009).
Metzger-Filho et al., "Management of metastatic HER2-positive breast cancer progression after adjuvant trastuzumab therapy—current evidence and future trends," Expert Opin. Investig. Drugs 19 Suppl 1:S31-S39 (2010).
Metzger-Filho et al., "Molecular targeted therapy in prevalent tumors: learning from the past and future perspectives," Current Clin. Pharmacol. 5(3):166-177 (2010).
Meyerhardt et al., "Phase II study of capecitabine, oxaliplatin, and erlotinib in previously treated patients with metastastic colorectal cancer," J. Clin. Oncol. 24(12):1892-1897 (2006).
Minami et al., "The major lung cancer-derived mutants of ERBB2 are oncogenic and are associated with sensitivity to the irreversible EGFR/ERBB2 inhibitor HKI-272," Oncogene 26(34):5023-5027 (2007) (Epub Feb. 19, 2007).
Minkovsky and Berezov, "BIBW-2992, a dual receptor tyrosine kinase inhibitor for the treatment of solid tumors," Curr. Opin. Investig. Drugs 9(12):1336-1346 (2008).
Mitsudomi et al., "Biological and clinical implications of EGFR mutations in lung cancer," Int. J. Clin. Oncol. 11(3):190-198 (2006).
Moasser, "Targeting the function of the HER2 oncogene in human cancer therapeutics," Oncogene 26(46):6577-6592 (2007) (Epub May 7, 2007).
Morabito et al., "Methodological Issues of Clinical Research with EGFR Inhibitors," Curr. Cancer Ther. Rev. 3(4):292-302 (2007).
Moreno-Aspitia and Perez, "Treatment options for breast cancer resistant to anthracycline and taxane," Mayo Clin. Proc. 84(6):533-545 (2009).
Morozova et al., "System-level analysis of neuroblastoma tumor-initiating cells implicates AURKB as a novel drug target for neuroblastoma," Clin. Cancer Res. 16(18):4572-4582 (2010) (Epub Jul. 22, 2010).
Morris and Hudis, "Personalizing therapy for metastatic breast cancer," Expert Rev. Anticancer Ther. 9(9):1223-1226 (2009).
Morrow et al., "Recent advances in systemic therapy: Advances in systemic therapy for HER2-positive metastatic breast cancer," Breast Cancer Res. 11(4):207 (2009) (Epub Jul. 15, 2009).
Mukai, "Targeted therapy in breast cancer: current status and future directions," Jpn. J. Clin. Oncol. 40(8):711-716 (2010) (Epub Apr. 8, 2010).
Mukai, "Treatment strategy for HER2-positive breast cancer," Int. J. Clin. Oncol. 15(4):335-340 (2010) (Epub Jul. 15, 2010).
Mukherji and Spicer, "Second-generation epidermal growth factor tyrosine kinase inhibitors in non-small cell lung cancer," Expert Opin. Investig. Drugs 18(3):293-301 (2009).
Mullard, "2010 in Reflection," Nat. Rev. Drug Discov. 10:7-9 (2011).
Munagala et al., "Promising molecular targeted therapies in breast cancer," Indian J. Pharmacol. 43(3):236-245 (2011).
Mundhenke et al., "Significance of Tyrosine Kinase Inhibitors in the Treatment of Metastatic Breast Cancer," Breast Care (Basel) 4(6):373-378 (2009) (Epub Nov. 16, 2009).
Murphy and Fornier, "HER2-positive breast cancer: beyond trastuzumab," Oncology (Williston Park) 24(5):410-415 (2010).
Muthuswamy, "Trastuzumab resistance: all roads lead to SRC," Nat. Med. 17(4):416-418 (2011).
Nagata et al., "PTEN activation contributes to tumor inhibition by trastuzumab, and loss of PTEN predicts trastuzumab resistance in patients," Cancer Cell vol. 6(2):117-127 (2004).
Nahta and O'Regan, "Evolving strategies for overcoming resistance to HER2-directed therapy: targeting the PI3K/Akt/mTOR pathway," Clin. Breast Cancer 10 Suppl 3:S72-S78 (2010).
Nakagawa et al., "Combined therapy with mutant-selective EGFR inhibitor and Met kinase inhibitor for overcoming erlotinib resistance in EGFR-mutant lung cancer," 11(10):2149-2157 (2012) (Epub Jul. 25, 2012).
Natoli et al., "Tyrosine kinase inhibitors," Curr. Cancer Drug Targets 10(5):462-483 (2010).
Nguyen et al., "Acquired resistance to epidermal growth factor receptor tyrosine kinase inhibitors in non-small-cell lung cancers dependent on the epidermal growth factor receptor pathway," Clin. Lung Cancer 10(4):281-289(2009).

(56) References Cited

OTHER PUBLICATIONS

Nicholson et al., "EGFR and cancer prognosis," Eur. J. Cancer 37 Suppl 4:S9-S15 (2001).
Nielsen et al., "HER2-targeted therapy in breast cancer. Monoclonal antibodies and tyrosine kinase inhibitors," Cancer Treat Rev. 35(2):121-136 (2009) (Epub Nov. 12, 2008).
Nitz, "Perspectives: Other ErbB2-Targeted Therapies," Breast Care (Basel) 5(s1):25-27 (2010) (Epub Apr. 26, 2010).
Nolè et al., "Dose-finding and pharmacokinetic study of an all-oral combination regimen of oral vinorelbine and capecitabine for patients with metastatic breast cancer," Ann. Oncol. 17(2):322-329 (2006) (Epub Nov. 22, 2005).
O'Brien et al., "Activated phosphoinositide 3-kinase/AKT signaling confers resistance to trastuzumab but not lapatinib," Mol. Cancer Ther. 9(6):1489-1502 (2010) (Epub May 25, 2010).
Ocaña and Amir, "Irreversible pan-ErbB tyrosine kinase inhibitors and breast cancer: current status and future directions," Cancer Treat. Rev. 35(8):685-691 (2009) (Epub Sep. 4, 2009).
Ocaña and Pandiella, "Identifying breast cancer druggable oncogenic alterations: lessons learned and future targeted options," Clin. Cancer Res. 14(4):961-970 (2008).
Ocaña et al., "New Targeted Therapies in Head and Neck Cancer," Cancer Chemo. Rev. 4:35-43 (2009).
Ocaña et al., "Novel tyrosine kinase inhibitors in the treatment of cancer," Curr. Drug Targets 10(6):575-576 (2009).
Ocaña et al., "Preclinical development of molecular-targeted agents for cancer," Nat. Rev. Clin. Oncol. 8:200-209 (2011).
Office Action dated May 26, 2010 issued in corresponding European Patent Application No. 06836862.0.
Office Action dated Oct. 28, 2013 issued in corresponding Japanese Patent Application No. 2012-179873.
Office Action issued in corresponding Pakistan Patent Application No. 1456/2006 dated 2007.
Official Action and Search Report with English Translation, dated Jun. 18, 2013, for corresponding Chinese Application No. 201210328133.2.
Oh et al., "Detection of epidermal growth factor receptor in the serum of patients with cervical carcinoma," Clin. Cancer Res. 6(12):4760-4763 (2000).
O'Hare et al., "Bcr-Abl kinase domain mutations and the unsettled problem of Bcr-AblT315I: looking into the future of controlling drug resistance in chronic myeloid leukemia," Clin. Lymphoma Myeloma 7 Suppl 3:S120-S130 (2007).
Omuro et al., "Lessons learned in the development of targeted therapy for malignant gliomas," Mol. Cancer Ther. 6(7):1909-1919 (2007).
O'Neil et al., (ed.). The Merck Index—An Encyclopedia of Chemicals, Drugs, and Biologicals. 13th Edition, Whitehouse Station, NJ: Merck and Co., Inc., 2001., p. 1454-1455.
Oshima, "Crystallization of Polymorphs and Pseudo-Polymorphs and Its Control," Pharm. Stage 6(10):48-53 (2007). [English Translation Not Available].
Ostro and Cullis, "Use of liposomes as injectable-drug delivery systems," Am. J. Hosp. Pharm. 46(8):1576-1587 (1989).
Ouchi et al., "Antitumor activity of erlotinib in combination with capecitabine in human tumor xenograft models," Cancer Chemother. Pharmacol. 57(5):693-702 (2006).
Pal et al., "Targeted therapies for non-small cell lung cancer: an evolving landscape," Mol. Cancer Ther. 9(7):1931-1944 (2010) (Epub Jun. 22, 2010).
Pallis et al., "Targeted therapies in the treatment of advanced/metastatic NSCLC," Eur. J. Cancer 45(14):2473-2487 (2009).
Pantuck et al., "Prognostic relevance of the mTOR pathway in renal cell carcinoma: implications for molecular patient selection for targeted therapy," Cancer 109(11):2257-2267 (2007).
Pao and Chmielecki, "Rational, biologically based treatment of EGFR-mutant non-small-cell lung cancer," Nat. Rev. Cancer 10(11):760-774 (2010) (Epub Oct. 22, 2010).
Pao, "Defining clinically relevant molecular subsets of lung cancer," Cancer Chemother. Pharmacol. 58(Suppl 1):s11-s15 (2006).

Papaldo et al., "A phase II study on metastatic breast cancer patients treated with weekly vinorelbine with or without trastuzumab according to HER2 expression: changing the natural history of HER2-positive disease," Ann. Oncol. 17(4):630-636 (2006) (Epub Jan. 12, 2006).
Parideans et al., "Neratinib (HKI-272), an irreversible pan-ErbB receptor tyrosine kinase inhibitor: Phase 2 results in patients with ErbB2+ advanced breast cancer," Ann. Oncol. 20(Suppl 2):ii61-ii62 Abstr. 186P (2009).
Parkin and Fernández, "Use of statistics to assess the global burden of breast cancer," Breast J. 12(Suppl 1):S70-S80 (2006).
Pegram et al., "Expert roundtable: emerging questions in ErbB2-positive breast cancer; Feb. 22, 2007," Clin. Breast Cancer 8(Suppl 3):S131-S141 (2008).
Pegram et al., "The molecular and cellular biology of HER2/neu gene amplification/overexpression and the clinical development of herceptin (trastuzumab) therapy for breast cancer," Cancer Treat. Res. 103:57-75 (2000).
Perez et al., "Updated Results of the Combined Analysis of NCCTG N9831 and NSABP B-31 Adjuvant Chemotherapy With/Without Trastuzumab in Patients with HER2-Positive Breast Cancer," J. Clin. Oncol. ASCO Annual Meeting Proc. 25(18S):512 (2007).
Pérez-Soler, "Individualized therapy in non-small-cell lung cancer: future versus current clinical practice," Oncogene 28(Suppl 1):S38-S45 (2009).
Pérez-Tenorio et al., "PIK3CA mutations and PTEN loss correlate with similar prognostic factors and are not mutually exclusive in breast cancer," Clin. Cancer Res. 13(12):3577-3584 (2007).
Perren et al., "Immunohistochemical evidence of loss of PTEN expression in primary ductal adenocarcinomas of the breast," Am. J. Pathol. 155(4):1253-1260 (1999).
Petter et al., "A novel small-molecule drug platform to silence cancer targets—application to the panErbB kinases," In: Proceedings of the 100th Annual Meeting of the American Association for Cancer Research; Apr. 18-22, 2009; Denver, CO. Abstr. 3746 (2009).
Pfister et al., "American Society of Clinical Oncology Clinical Practice Guideline for the Use of Larynx-Preservation Strategies in the Treatment of Laryngeal Cancer," J. Clin. Oncol. 24(22):3693-3704 (2006) (Epub Jul. 10, 2006).
Piccart et al., "Beyond trastuzumab: new anti-HER2 agents," Breast 20(Suppl 1):S1-52 Abstr. S02 (2011).
Piccart, "Circumventing de novo and acquired resistance to trastuzumab: new hope for the care of ErbB2-positive breast cancer," Clin. Breast Cancer 8(Suppl 3):S100-S113 (2008).
Plati et al., "Dysregulation of apoptotic signaling in cancer: molecular mechanisms and therapeutic opportunities," J. Cell. Biochem. 104(4):1124-1149 (2008).
Plosker and Keam, "Trastuzumab: a review of its use in the management of HER2-positive metastatic and early-stage breast cancer," Drugs 66(4):449-475 (2006).
Ponz-Sarvisé et al., "Epidermal growth factor receptor inhibitors in colorectal cancer treatment: what's new?" World J. Gastroenterol. 13(44):5877-5887 (2007).
Potashman and Duggan, "Covalent modifiers: an orthogonal approach to drug design," J. Med. Chem. 52(5):1231-1246 (2009).
Rabindran et al., "Antitumor activity of HKI-272, an orally active, irreversible inhibitor of the HER-2 tyrosine kinase," Cancer Res. 64(11):3958-3965 (2004).
Rabindran, "Antitumor activity of HER-2 inhibitors," Cancer Lett. 227(1):9-23 (2005) (Epub Dec. 15, 2004).
Raines and Ross, "Multiple growth factors are associated with lesions of atherosclerosis: specificity or redundancy?" Bioessays 18(4):271-282 (1996).
Rampaul et al., "Clinical value of epidermal growth factor receptor expression in primary breast cancer," Adv. Anat. Pathol. 12(5):271-273 (2005).
Rana and Swaby, "Targeted Therapies for HER2 Breast Cancer: A View of the Landscape," Curr. Breast Cancer Rep. 3:55-62 (2011).
Ranganathan and Muneer, "Highlights from: The 24th Annual Meeting of the American Association for Cancer Research; Los Angeles, CA; Apr. 14-18, 2007," Clin. Lung Cancer 8(6):359-363 (2007).

(56) References Cited

OTHER PUBLICATIONS

Rao, "Recent developments of collagen-based materials for medical applications and drug delivery systems," J. Biomater Sci. Polym. Ed. 7(7):623-645 (1995).

Ray et al., "Lung cancer therapeutics that target signaling pathways: an update," Expert Rev. Respir. Med. 4(5):631-645 (2010).

Ray et al., "The role of EGFR inhibition in the treatment of non-small cell lung cancer," Oncologist 14(11):1116-1130 (2009) (Epub Nov. 5, 2009).

Redon et al., "A simple specific pattern of chromosomal aberrations at early stages of head and neck squamous cell carcinomas: PIK3CA but not p63 gene as a likely target of 3q26-qter gains," Cancer Res. 61(10):4122-4129 (2001).

Reid et al., "Dual inhibition of ErbB1 (EGFR/HER1) and ErbB2 (HER2/neu)," Eur. J. Cancer 43(3):481-489 (2007) (Epub Jan. 8, 2007).

Response filed by Applicant on Apr. 30, 2009 to Office Action dated Jul. 18, 2008, in corresponding European Patent Application No. 06836862.0.

Rewcastle et al., "Synthesis of 4-(phenylamino)pyrimidine derivatives as ATP-competitive protein kinase inhibitors with potential for cancer chemotherapy," Curr. Org. Chem. 4(7):679-706 (2000).

Rexer et al., "Overcoming resistance to tyrosine kinase inhibitors: lessons learned from cancer cells treated with EGFR antagonists," Cell Cycle 8(1):18-22 (2009) (Epub Jan. 30, 2009).

Rich et al., "Phase II trial of gefitinib in recurrent glioblastoma," J. Clin. Oncol. 22(1):133-142 (2004) (Epub Nov. 24, 2003).

Riely et al., "Update on epidermal growth factor receptor mutations in non-small cell lung cancer,". Clin. Cancer Res. 12(24):7232-7241 (2006).

Riely, "Second-generation epidermal growth factor receptor tyrosine kinase inhibitors in non-small cell lung cancer," J. Thorac. Oncol. 3(6 Suppl 2):S146-S149 (2008).

Rosell et al., "Age-related genetic abnormalities: the Achilles' heel for customizing therapy in elderly lung cancer patients," Personalized Medicine 4(1):59-72 (2007).

Rosell et al., "Screening for epidermal growth factor receptor mutations in lung cancer," N. Engl. J. Med. 361(10):958-967 (2009) (Epub Aug. 19, 2009).

Rosell et al., "Treatment of non-small-cell lung cancer and pharmacogenomics: where we are and where we are going," Curr. Opin. Oncol. 18(2):135-143 (2006).

Rosen et al., "Targeting signal transduction pathways in metastatic breast cancer: a comprehensive review," Oncologist 15(3):216-235 (2010) (Epub Mar. 3, 2010).

Rotella, "Medicinal Chemistry—XXth International Symposium. Lead finding strategies and kinase selectivity," IDrugs 11(11):774-778 (2008).

Roukos, "Trastuzumab and beyond: sequencing cancer genomes and predicting molecular networks," Pharmacogenomics J. 11(2):81-92 (2011) (Epub Oct. 26, 2010).

Roy and Perez, "Beyond trastuzumab: small molecule tyrosine kinase inhibitors in HER-2-positive breast cancer," Oncologist 14(11):1061-1069 (2009) (Epub Nov. 3, 2009).

Rubin et al., "10q23.3 loss of heterozygosity is higher in lymph node-positive (pT2-3,N+) versus lymph node-negative (pT2-3,N0) prostate cancer," Hum. Pathol. 31(4):504-508 (2000).

Rudloff and Samuels, "A growing family: adding mutated Erbb4 as a novel cancer target," Cell Cycle. 9(8):1487-1503 (2010) (Epub Apr. 15, 2010).

Saal et al., "PIK3CA mutations correlate with hormone receptors, node metastasis, and ERBB2, and are mutually exclusive with PTEN loss in human breast carcinoma," Cancer Res. 65(7):2554-2559 (2005).

Sakamoto et al., "Su-11248 Sugen," Curr. Opin. Investig. Drugs 5(12):1329-1339 (2004).

Salvesen et al., "Integrated genomic profiling of endometrial carcinoma associates aggressive tumors with indicators of PI3 kinase activation," Proc. Natl. Acad. Sci. U.S.A. 106(12):4834-4839 (2009) (Epub Mar. 4, 2009).

Samuels and Ericson, "Oncogenic PI3K and its role in cancer," Curr. Opin. Oncol. 18(1):77-82 (2006).

Sanchez-Martin and Pandiella, "Differential action of ErbB kinase inhibitors on receptor oligomerization," EJC Suppl. 8:107 Abstr. 337 (2010).

Santarpia et al., "Tyrosine kinase inhibitors for non-small-cell lung cancer: finding patients who will be responsive," Expert Rev. Respir. Med. (3):413-424 (2011).

Sartore-Bianchi et al., "Rationale and clinical results of multi-target treatments in oncology," Int. J. Biol. Markers 22(1 Suppl 4):S77-S87 (2007).

Sathornsumetee et al., "Malignant glioma drug discovery—targeting protein kinases," Expert Opin. Drug Discov. 2(1):1-17 (2007).

Sattler et al., "EGFR-targeted therapeutics: focus on SCCHN and NSCLC," ScientificWorldJournal 8:909-919 (2008).

Saura et al., "Safety of Neratinib (HKI-272) in Combination with Capecitabine in Patients with Solid Tumors: A Phase 1/2 Study," Cancer Res. 69(24 Suppl) Abstr. 5108 (2009).

Saura et al., "The safety of Neratinib (HKI-272) in Combination with Capecitabine in Patients with Solid Tumors: A Phase 1/2 Study," Ann. Oncol. 21(Suppl 4):iv63 Abstr. 147P (2010).

Saura et al., (Dec. 2011). Safety and Efficacy of Neratinib in Combination with Capecitabine in Patients with ErbB2-Positive Breast Cancer. Poster presented at the 2011 CTRC-AACR San Antonio Breast Cancer Symposium, San Antonio, Texas.

Scaltriti et al., "Expression of p95HER2, a truncated form of the HER2 receptor, and response to anti-HER2 therapies in breast cancer," J. Natl. Cancer Inst. 99(8):628-638 (2007).

Schiller et al., "Comparison of four chemotherapy regimens for advanced non-small-cell lung cancer," N. Engl. J. Med. 346(2):92-98 (2002).

Scott and Salgia, "Biomarkers in lung cancer: from early detection to novel therapeutics and decision making," Biomark. Med. 2(6):577-586 (2008).

Sebastian et al., "The complexity of targeting EGFR signalling in cancer: from expression to turnover," Biochim. Biophys. Acta. 1766(1):120-139 (2006) (Epub Jun. 23, 2006).

Sequist and Dziadziuszko, "Update on epidermal growth factor receptor inhibitor development in lung cancer," J. Thorac. Oncol. 1(7):740-743 (2006).

Sequist et al., "Neratinib, an irreversible pan-ErbB receptor tyrosine kinase inhibitor: results of a phase II trial in patients with advanced non-small-cell lung cancer," J. Clin. Oncol. 28(18):3076-3083 (2010) (Epub May 17, 2010).

Sequist, "Second-generation epidermal growth factor receptor tyrosine kinase inhibitors in non-small cell lung cancer," Oncologist 12(3):325-330 (2007).

Settleman and Kurie, "Drugging the bad "AKT-TOR" to overcome TKI-resistant lung cancer," Cancer Cell 12(1):6-8 (2007).

Seyhan et al., "A genome-wide RNAi screen identifies novel targets of neratinib sensitivity leading to neratinib and paclitaxel combination drug treatments," Mol. Biosyst. 7(6):1974-1989 (2011) (Epub Apr. 12, 2011).

Sharma and Jayanth, "Neratinib, an irreversible erbB receptor tyrosine Kinase inhibitor, in patients with advanced erbB2-positive breast cancer," [commentary] Adv. Breast Cancer 7(1):21 (2010).

Sharma and Settleman, "Oncogene addiction: setting the stage for molecularly targeted cancer therapy," Genes Dev. 21(24):3214-3231 (2007).

Sharma et al., "Epidermal growth factor receptor mutations in lung cancer," Nat. Rev. Cancer7(3):169-181 (2007).

Sharma et al., "Receptor tyrosine kinase inhibitors as potent weapons in war against cancers," Curr. Pharm. Des. 15(7):758-776 (2009).

Shaw et al., "Pharmacological Inhibition of Restenosis: Learning From Experience," Trends Pharmacol. Sci. 16(12):401-404 (1995).

Shawver et al., "Receptor Tyrosine Kinases as Targets for Inhibition of Angiogenesis," Drug Discov. Today 2(2):50-63 (1997).

Shayesteh et al., "PIK3CA is implicated as an oncogene in ovarian cancer," Nat. Genet. 21(1):99-102 (1999).

Shimamura and Shapiro, "Heat shock protein 90 inhibition in lung cancer," J. Thorac. Oncol. 3(6 Suppl 2):S152-S159 (2008).

(56) References Cited

OTHER PUBLICATIONS

Shimamura et al., "Hsp90 inhibition suppresses mutant EGFR-T790M signaling and overcomes kinaseinhibitor resistance," Cancer Res. 68(14):5827-5838 (2008).

Shimamura et al., "on-small-cell lung cancer and Ba/F3 transformed cells harboring the ERBB2 G776insV_G/C mutation are sensitive to the dual-specific epidermal growth factor receptor and ERBB2 inhibitor HKI-272," Cancer Res. 66(13):6487-6491 (2006).

Sibilia et al., "The epidermal growth factor receptor: from development to tumorigenesis," Differentiation 75(9):770-787 (2007).

Sigal, "Basic science for the clinician 48: tyrosine kinases in disease: the potential for inhibitors in the treatment of immunologic diseases," J. Clin. Rheumatol. 14(1):45-48 (2008).

Simon et al., "By 1023/SK&F 96022: biochemistry of a novel (H++K+)-ATPase inhibitor," Biochem Pharmacol. 39(11):1799-1806 (1990).

Singh et al., "Targeted covalent drugs of the kinase family," Curr. Opin. Chem. Biol. 14(4):475-480 (2010) (Epub Jul. 6, 2010).

Singh et al., "The resurgence of covalent drugs," Nat. Rev. Drug Discov. 10(4):307-317 (2011).

Slamon et al., "BCIRG 006: 2nd interim analysis phase III randomized trial comparing doxorubicin and cyclophosphamide followed by docetaxel (AC-T) with doxorubicin and cyclophosphamide followed by docetaxel and trastuzumab (AC-TH) with docetaxel, carboplatin and trastuzumab (TCH) in Her2neu positive early breast cancer patients," In: San Antonio breast cancer symposium; 2006 [abstract 52].

Slamon et al., "Human breast cancer: correlation of relapse and survival with amplification of the HER-2/neu oncogene," Science 235(4785):177-182 (1987).

Smith et al. "2006 update of recommendations for the use of white blood cell growth factors: an evidence-based clinical practice guideline,"J. Clin. Oncol. 24(19):3187-3205 (2006) (Epub May 8, 2006).

Smith et al., "2-year follow-up of trastuzumab after adjuvant chemotherapy in HER2-positive breast cancer: a randomised controlled trial." Lancet 369(9555):29-36 (2007).

Smith, "Goals of Treatment of Patients with Metastatic Breast Cancer," Semin. Oncol. 33:S2-S5 (2006).

Solca et al., "Beyond Trastuzumab: Second-Generation Targeted Therapies for HER-2-Positive Breast Cancer," Drugs for HER-2-Positive Breast Cancer, Milestones in Drug Therapy, 2011 p. 91-107 (2011).

Specht and Gralow, "Neoadjuvant chemotherapy for locally advanced breast cancer," Semin. Radiat. Oncol. 9(4):222-228 (2009).

Spector et al., "Small Molecule HER-2 Tyrosine Kinase Inhibitors," Breast Cancer Res. 9(2):205 (2007).

Spector, "Treatment of metastatic ErbB2-positive breast cancer: options after progression on trastuzumab," Clin. Breast Cancer 8 Suppl 3:S94-S99 (2008).

Spicer and Rudman, "EGFR inhibitors in non-small cell lung cancer (NSCLC): the emerging role of the dual irreversible EGFR/HER2 inhibitor BIBW 2992," Target Oncol. 5(4):245-255 (2010) (Epub Jun. 24, 2010).

Srivastava et al., "Synthesis and structure-activity relationships of potent antitumor active quinoline and naphthyridine derivatives," Anticancer Agents Med. Chem. 7(6):685-709 (2007).

Staroslawska et al. (Dec. 2010). Safety and Efficacy of Neratinib (HKI-272) Plus Vinorelbine in the Treatment of Patients With ErbB2+ Metastatic Breast Cancer Pretreated With Anti-Her2 Therapy. Poster presented at teh 33rd Annual San Antonio Breast Cancer Symposium, San Antonio, Texas.

Stebbing et al., "Lemur tyrosine kinase-3 (LMTK3) in cancer and evolution," Oncotarget 2(6):428-429 (2011).

Steck et al., "Identification of a candidate tumour suppressor gene, MMAC1, at chromosome 10q23,3 that is mutated in multiple advanced cancers," Nat. Genet. 15(4):356-362 (1997).

Steins et al., "Targeting the epidermal growth factor receptor in non-small cell lung cancer," Onkologie 33(12):704-709 (2010) (Epub Nov. 26, 2010).

Stemke-Hale et al., "An integrative genomic and proteomic analysis of PIK3CA, PTEN, and AKT mutations in breast cancer," Cancer Res. 68(15):6084-6091 (2008).

Stokoe et al., "Dual role of phosphatidylinositol-3,4,5-trisphosphate in the activation of protein kinase B," Science 277(5325):567-570 (1997).

Sugiyama, "Drug Transporters: Roles in New Drug Discovery and Development," Drug Metab. Rev. 42(S1):1-323 (2010).

Suzuki et al., "Combination of trastuzumab and vinorelbine in metastatic breast cancer," Jpn. J. Clin. Oncol. 33(10):514-517 (2003).

Swaby et al., "Neratinib in combination with trastuzumab for the treatment of advanced breast cancer: A phase I/II study," J. Clin. Oncol. 27:15s(suppl; abstr 1004) (2009).

Tagliabue et al., "HER2 as a target for breast cancer therapy," Expert Opin. Biol. Ther. 10(5):711-724 (2010).

Takada, "API Form Screening and Selection in Drug Discovery Stage," Pharm Stage 6(10):20-25 (2007). [English Translation Not Available].

Tejpar et al., "Phase 1/2a study of EKB-569, an irreversible inhibitor of epidermal growth factor receptor, in combination with 5-fluorouracil, leucovorin, and oxaliplatin (FOLFOX-4) in patients with advanced colorectal cancer (CRC)," J. Clin. Oncol. 22(14S):264s Abstr. 3579 (2004).

Test Procedures and Acceptance Criteria for New Drug Substances and New Drug Products; Pharmaceutical Affairs Bureau Notification No. 568; 2001 [English Translation Not Available].

Therasse et al., "New guidelines to evaluate the response to treatment in solid tumors. European Organization for Research and Treatment of Cancer, National Cancer Institute of the United States, National Cancer Institute of Canada," J. Natl. Cancer Inst. 92(3):205-216 (2000).

Tjin Tham Sjin et al., "Design of a novel covalent EGFR mutant-selective inhibitor," EJC Suppl. 8(7):31 Abstr. 73 (2010).

Toffoli et al., "Pharmacology of epidermal growth factor inhibitors," Int. J. Biol. Markers 22(1 Suppl 4):S24-S39 (2007).

Tolaney and Krop, "Mechanisms of trastuzumab resistance in breast cancer," Anticancer Agents Med. Chem. 9(3):348-355 (2009).

Tolaney et al., "HER2-Positive Breast Cancer," JCOM 14(7):395-403 (2007).

Tomillero and Moral, "Gateways to Clinical Trials," Methods Find. Exp. Clin. Pharmacol. 31(3):183-226 (2009).

Tomillero and Moral, "Gateways to Clinical Trials," Methods Find. Exp. Clin. Pharmacol. 31(10):661-700 (2009).

Tookman and Roylance, "New Drugs for Breast Cancer," Br. Med. Bull. 96:111-129 (2010) (Epub Sep. 23, 2010).

Torres and Harris, "Polycystic kidney disease: genes, proteins, animal models, disease mechanisms and therapeutic opportunities," J. Intern. Med. 261(1):17-31 (2007).

Traxler, "Tyrosine kinase inhibitors in cancer treatment (Part II)," Exp. Opin. Ther. Patents 8(12):1599-1625 (1998).

Tsou et al., "Optimization of 6,7-Disubstituted-4-(Arylamino)Quinoline-3-Carbonitriles as Orally Active, Irreversible Inhibitors of Human Epidermal Growth Factor Receptor-2 Kinase Activity," J. Med. Chem. 48(4):1107-1131 (2005).

Tsou, "American Chemical Society—226th National Meeting. Novel Substituted 4-Anilinoquinoline-3-carbonitriles as orally active, irreversible binding inhibitors of HER-2 Kinase," (abstr. 14) 2003.

Twelves et al., "Erlotinib in combination with capecitabine and docetaxel in patients with metastatic breast cancer: a dose-escalation study," Eur. J. Cancer 44(3):419-426 (2008) (Epub Jan. 30, 2008).

Ullrich et al., "Human epidermal growth factor receptor cDNA sequence and aberrant expression of the amplified gene in A431 epidermoid carcinoma cells," Nature 309(5967):418-425 (1984).

Untch, "Targeted Therapy for Early and Locally Advanced Breast Cancer," Breast Care (Basel) 5(3):144-152 (2010) (Epub Jun. 16, 2010).

Upeslacis, Janis, Meeting at Mcgill University, Canada, Evolution of Kinase Inhibitors at Wyeth, Oct. 16, 2002.

Van Arnum, "Evaluating late-stage pipelines and potential: will 2011 be a more promising year for new molecular entities? A review

(56) References Cited

OTHER PUBLICATIONS of Big Pharma's late-stage pipeline shows what might lie ahead." Pharmaceutical Technology 35.2 (2011): 52+. Expanded Academic ASAP. Web. Jul. 18, 2011.
Van Schaeybroeck et al., "Epidermal growth factor receptor activity determines response of colorectal cancer cells to gefitinib alone and in combination with chemotherapy," Clin. Cancer Res. 11(20):7480-7489 (2005).
Vasudevan et al., "AKT-independent signaling downstream of oncogenic PIK3CA mutations in human cancer," Cancer Cell 16(1):21-32 (2009).
Vazquez et al., "HER2-Positive Breast Cancer: Analysis of Efficacy in Different Groups," Cancer Chemother. Rev. 4(4):224-240 (2009).
Vincent et al., "Anticancer efficacy of the irreversible EGFr tyrosine kinase inhibitor PD 0169414 against human tumor xenografts," Cancer Chemother. Pharmacol. 45(3):231-238 (2000).
Vivanco and Mellinghoff, "Epidermal growth factor receptor inhibitors in oncology," Curr. Opin. Oncol. 22(6):573-578 (2010).
Von Eyben, "Epidermal growth factor receptor inhibition and non-small cell lung cancer," Crit. Rev. Clin. Lab. Sci. 43(4):291-323 (2006).
Vora et al., "Novel Therapeutics in Breast Cancer—Looking to the Future," Update on Cancer Therapeutics 3:189-205 (2009).
Wagner and Kaufmann, "Prospects for the Use of ATR Inhibitors to Treat Cancer," Pharmaceuticals 3:1311-1334 (2010).
Walko and Lindley, "Capecitabine: a review," Clin. Ther. 27(1):23-44 (2005).
Wang et al., "Characterization of HKI-272 covalent binding to human serum albumin," Drug Metab. Dispos. 38(7):1083-1093 (2010) (Epub Apr. 16, 2010).
Ware et al., "A mechanism of resistance to gefitinib mediated by cellular reprogramming and the acquisition of an FGF2-FGFR1 autocrine growth loop," Oncogenesis 2:e39 (2013).
Weber, "Toward a molecular classification of cancer," Toxicology Dec. 5, 2010;278(2):195-198 (2010) (Epub Oct. 24, 2009).
Wen and Drappatz, "Novel therapies for meningiomas," Expert Rev. Neurother. 6(10):1447-1464 (2006).
Wheatley-Price and Shepherd, "Epidermal growth factor receptor inhibitors in the treatment of lung cancer: reality and hopes," Curr. Opin. Oncol. 20(2):162-175 (2008).
Whenham et al., "HER2-positive breast cancer: from trastuzumab to innovatory anti-HER2 strategies," Clin. Breast Cancer 8(1):38-49 (2008).
Wickham, "Evolving treatment paradigms for chemotherapy-induced nausea and vomiting," Cancer Control 19(2 Suppl):3-9 (2012).
Widakowich et al., "HER-2 positive breast cancer: what else beyond trastuzumab-based therapy?" Anticancer Agents Med. Chem. 8(5):488-496 (2008).
Widakowich et al., "Molecular targeted therapies in breast cancer: where are we now?" Int. J. Biochem. Cell. Biol. 2007;39(7-8):1375-1387 (2007) (Epub May 4, 2007).
Wissner and Mansour, "The development of HKI-272 and related compounds for the treatment of cancer," Arch. Pharm. (Weinheim) 341(8):465-477 (2008).
Wissner et al., "Dual irreversible kinase inhibitors: quinazoline-based inhibitors incorporating two independent reactive centers with each targeting different cysteine residues in the kinase domains of EGFR and VEGFR-2," Bioorg. Med. Chem. 15(11):3635-4368 (2007) (Epub Mar. 23, 2007).
Woenckhaus et al., "Prognostic value of PIK3CA and phosphorylated AKT expression in ovarian cancer," Virchows Arch. 450(4):387-395 (2007) (Epub Feb. 15, 2007).
Wondrak, "Redox-directed cancer therapeutics: molecular mechanisms and opportunities," Antioxid. Redox Signal. 11(12):3013-3069 (2009).
Wong et al., "A phase I study with neratinib (HKI-272), an irreversible pan ErbB receptor tyrosine kinase inhibitor, in patients with solid tumors," Clin. Cancer Res. 15(7):2552-2558 (2009) (Epub Mar. 24, 2009).
Wong et al., "HKI-272, an irreversible pan ErbB receptor tyrosine kinase inhibitory: Preliminary phase 1 results in patients with solid tumors," J. Clin. Oncol. 24(18S):125s Abstr. 3018 (2006).
Wong, "HKI-272 in non small cell lung cancer," Clin. Cancer Res. 13(15 Pt 2):4593s-4596s (2007).
Wong, "Searching for a magic bullet in NSCLC: the role of epidermal growth factor receptor mutations and tyrosine kinase inhibitors," Lung Cancer 60(Suppl 2):S10-S18 (2008).
World Health Organization (2008). *Fact Sheet—Cancer*, No. 297, 2008. Retrieved from http://www.who.int/mediacentre/factsheets/fs297/en/.
World Health Organization (2008).*World Health Statistics*, 2008. Retrieved from http://www.who.int/gho/publications/world_health_statistics/EN_WHS08_Full.pdf?ua=1.
Written Opinion of the International Searching Authority for International Application No. PCT/US2009/047643 dated Dec. 17, 2010.
Wu et al., "Design and synthesis of tetrahydropyridothieno[2,3-d]pyrimidine scaffold based epidermal growth factor receptor (EGFR) kinase inhibitors: the role of side chain chirality and Michael acceptor group for maximal potency," J. Med. Chem. 53(20):7316-7326 (2010).
Wu et al., "Somatic mutation and gain of copy number of PIK3CA in human breast cancer," Breast Cancer Res. 7(5):R609-R616 (2005) (Epub May 31, 2005).
Wu et al., "TAK-285, a Novel HER2/EGFR Inhibitor, Penetrates the CNS in Rats with an Intact Blood Brain Barrier (BBB),"Cancer Res. 69(24 Suppl): Abstr. 5098 (2009).
Wu et al., "Uncommon mutation, but common amplifications, of the PIK3CA gene in thyroid tumors," J. Clin. Endocrinol. Metab. 90(8):4688-4693 (2005) (Epub May 31, 2005).
Wykosky et al., "Therapeutic targeting of epidermal growth factor receptor in human cancer: successes and limitations," Chin. J. Cancer 30(1):5-12 (2011).
Xia et al., "Truncated ErbB2 receptor (p95ErbB2) is regulated by heregulin through heterodimer formation with ErbB3 yet remains sensitive to the dual EGFR/ErbB2 kinase inhibitor GW572016," Oncogene 23(3):646-653 (2004).
Xu et al., "Acquired resistance of lung adenocarcinoma to EGFR-tyrosine kinase inhibitors gefitinib and erlotinib," Cancer Biol. Ther. 9(8):572-582 (2010) (Epub Apr. 26, 2010).
Yamano, "Approach to Crystal Polymorph in Process Research of New Drug," Journal of Synthetic Organic Chemistry, Japan, 65(9):907-913 (2007). [English Translation Not Available].
Yang et al., "MicroRNA expression profiling in human ovarian cancer: miR-214 induces cell survival and cisplatin resistance by targeting PTEN," Cancer Res. 68(2):425-433 (2008).
Yano et al., "HGF-MET in Resistance to EGFR Tyrosine Kinase Inhibitors in Lung Cancer," Curr. Signal Transduct. Ther. 6(2):228-233 (2011).
Yim et al., "Rak functions as a tumor suppressor by regulating PTEN protein stability and function," Cancer Cell 15(4):304-314 (2009).
Yoshida et al., "Targeting epidermal growth factor receptor: central signaling kinase in lung cancer," Biochem. Pharmacol. 80(5):613-623 (2010) (Epub May 24, 2010).
Yoshimura et al., "EKB-569, a new irreversible epidermal growth factor receptor tyrosine kinase inhibitor, with clinical activity in patients with non-small cell lung cancer with acquired resistance to gefitinib," Lung Cancer 51(3):363-368 (2006) (Epub Dec. 20, 2005).
Yuan and Cantley, "PI3K pathway alterations in cancer: variations on a theme," Oncogene 27(41):5497-5510 (2008).
Yun et al., "The T790M mutation in EGFR kinase causes drug resistance by increasing the affinity for ATP," Proc. Natl. Acad. Sci. U.S.A. 105(6):2070-2075 (2008) (Epub Jan. 28, 2008).
Yuza et al., "Allele-dependent variation in the relative cellular potency of distinct EGFR inhibitors," Cancer Biol. Ther. 6(5):661-667 (2007) (Epub Feb. 13, 2007).
Zaczek et al., "The diverse signaling network of EGFR, HER2, HER3 and HER4 tyrosine kinase receptors and the consequences for therapeutic approaches," Histol. Histopathol. 20(3):1005-1015 (2005).

(56) References Cited

OTHER PUBLICATIONS

Zagrekova et al., "Drug Treatment of Breast Cancer," Rossijskij Medicinskij Zhurnal 14:605 (2002). (English Translation Not Available).

Zahnow, "ErbB receptors and their ligands in the breast," Expert Rev. Mol. Med. 8(23):1-21 (2006).

Zhang et al. Xenograft Models of Breast Cancer: the Link between Characteristics of Biomarker Expression and the Anti-tumor Effect of the Representative Therapies [abstract]. In: Proceedings of the 101st Annual Meeting of the American Association for Cancer Research; Apr. 17-21, 2010; Washington, DC. Philadelphia (PA): AACR; Cancer Res 2010;70(8 Suppl):Abstract nr 647.

Zhang et al., "Advances in preclinical small molecules for the treatment of NSCLC," Expert Opin. Ther. Pat. 19(6):731-751 (2009).

Zhao et al., "Neratinib Reverses ATP-Binding Cassette B1-Mediaed Chemotherapeutic Drug Resistance in Vitro, in Vivo, and Ex-Vivo," Mol. Pharmacal. 82: 47-58 (2012).

Zhou et al., "Activation of the PTEN/Mtor/STAT3 Pathway in Breast Cancer Stem-Like Cells Is Required for Viability and Maintenance," Proc. Natl. Acad. Sci. U.S.A. 104:16158-16163 (2007).

Zhou et al., "EGFR Intron I Polymorphism in Asian Populations and Its Correlation with EGFR Gene Expression and Amplification in Breast Tumor Tissues," Cancer Biol. Ther. 5(11):1445-1449 (2006).

Zhou et al., "Novel Mutant-Selective EGFR Kinase Inhibitors Against EGFR T790M," Nature 462(7276):1070-1074 (2009).

Allen et al., "Potential benefits of the irreversible pan-erbB inhibitor, CI-1033, in the treatment of breast cancer," Semin. Oncol. 29(3 Suppl 11):11-21 (2002).

Avizienyte et al., "Comparison of the EGFR resistance mutation profiles generated by EGFR-targeted tyrosine kinase inhibitors and the impact of drug combinations," Biochem. J. 415(2):197-206 (2008).

Conte et al., "Evolving nonendocrine therapeutic options for metastatic breast cancer: how adjuvant chemotherapy influences treatment," Clin. Breast Cancer 7(11):841-849 (2007).

Erjala et al., "Concomitant chemoirradiation with vinorelbine and gefitinib induces additive effect in head and neck squamous cell carcinoma cell lines in vitro," Radiother. Oncol. 85(1):138-145 (2007).

Firoozinia et al., "PIK3CA gene amplification and PI3K p110α protein expression in breast carcinoma," Int. J. Med. Sci. 11(6):620-625 (2014).

Gilmer et al., "Impact of common epidermal growth factor receptor and HER2 variants on receptor activity and inhibition by lapatinib," Cancer Res. 68(2):571-579 (2008).

Goldhirsch et al., "2 years versus 1 year of adjuvant trastuzumab for HER2-positive breast cancer (HERA): an open-label, randomised control trail," Lancet 382:1021-1028 (2013).

Kulke et al., "Capecitabine Plus Erlotinib in Gemcitabine-Refractory Advanced Pancreatic Cancer," J. Clin. Oncol. 25(30):4787-4792 (2007).

McNeil et al., "Two targets, one drug for new EGFR inhibitors," J. Natl. Cancer Inst. 98(16):1102-1103 (2006).

Okumura et al., "Induction of Noxa Sensitizes Human Colorectal Cancer Cells Expressing Mcl-1 to the Small-Molecule Bcl-2/Bcl-xL Inhibitor, ABT-737," Clin. Cancer Res. 14(24):8132-8142 (2008).

Ross et al., "The HER-2 receptor and breast cancer: ten years of targeted anti-HER-2 therapy and personalized medicine," Oncologist 14:320-368 (2009).

Stockler et al., "Chemotherapy for advanced breast cancer—how long should it continue?" Breast Cancer Res. Treat. 81(Suppl. 1):S49-S52 (2003).

Vengerovsky, "Farmacologicheskaya nesovmestimost'," Bulleten' sibirskoi medicini 3:49-56 (2003). (English translation of Abstract provided).

Zhang et al., "Targeting cancer with small molecule kinase inhibitors," Nature 9:28-39 (2009).

Intellectual Property Office of Singapore Examination Report for Singapore Patent Application No. 2013046099 (dated Jan. 21, 2016).

Intellectual Property Office of Singapore Written Opinion for Singapore Patent Application No. 2013046099 (dated Jun. 4, 2015).

Official Action from corresponding Japanese Application JP 2012-279650, dated Apr. 22, 2014 [along with an English Translation, dated Jul. 16, 2014].

State Intellectual Property Office of the People's Republic of China Search Report for Chinese Patent Application No. 201210069340.0 (dated Dec. 11, 2015).

State Intellectual Property Office of the People's Republic of China Office Action for Chinese Patent Application No. 201210069340.0 (dated Dec. 21, 2015).

\* cited by examiner

ANTINEOPLASTIC COMBINATIONS WITH MTOR INHIBITOR, TRASTUZUMAB AND/OR HKI-272

CROSS REFERENCE TO RELATED APPLICATIONS

This application is a continuation of U.S. patent application Ser. No. 13/454,768, filed Apr. 24, 2012, which is a continuation of U.S. patent application Ser. No. 12/539,914, filed Aug. 12, 2009, which is a division of U.S. patent application Ser. No. 11/592,066, filed Nov. 2, 2006, which claims the benefit under 35 USC 119(e) of U.S. Provisional Patent Application No. 60/837,509, filed Aug. 14, 2006 and U.S. Provisional Patent Application No. 60/733,562, filed Nov. 4, 2005. The foregoing related applications, in their entirety, are incorporated herein by reference.

BACKGROUND OF THE INVENTION

This invention relates to the use of combinations of trastuzumab with an mTOR inhibitor and/or a HKI-272, for the treatment of neoplasms associated with overexpression or amplification of HER2.

CCI-779, rapamycin 42-ester with 3-hydroxy-2-(hydroxymethyl)-2-methylpropionic acid, is an ester of rapamycin which has demonstrated significant inhibitory effects on tumor growth in both in vitro and in vivo models. This compound is now known generically under the name temsirolimus. The preparation and use of hydroxyesters of rapamycin, including temsirolimus, are described in U.S. Pat. Nos. 5,362,718 and 6,277,983.

Temsirolimus exhibits cytostatic, as opposed to cytotoxic properties, and may delay the time to progression of tumors or time to tumor recurrence. Temsirolimus is considered to have a mechanism of action that is similar to that of sirolimus (rapamycin). Temsirolimus binds to and forms a complex with the cytoplasmic protein FKBP, which inhibits an enzyme, mTOR (mammalian target of rapamycin, also known as FKBP12-rapamycin associated protein [FRAP]). Inhibition of mTOR's kinase activity inhibits a variety of signal transduction pathways, including cytokine-stimulated cell proliferation, translation of mRNAs for several key proteins that regulate the G1 phase of the cell cycle, and IL-2-induced transcription, leading to inhibition of progression of the cell cycle from G1 to S. The mechanism of action of temsirolimus that results in the G1-S phase block is novel for an anticancer drug.

Metastatic breast cancer (MBC) is essentially incurable with standard therapy, and patients with MBC have a median survival of about 2 years after documentation of metastasis. As a consequence, the goals of treatment are to improve patients' symptoms while trying to maintain (or improve, in certain cases) quality of life. Prolonging survival remains a clear goal, particularly in breast cancer that has overexpression or amplification of the her-2 oncogene.

Herceptin® trastuzumab is an FDA-approved therapeutic monoclonal antibody for HER2 protein overexpressing metastatic breast cancer. A murine monoclonal antibody was described [see, U.S. Pat. No. 5,705,151]. The murine MAb4D5 molecule described in that document has been humanized in an attempt to improve its clinical efficacy by reducing immunogenicity and allowing it to support human effector functions. WO 92/22653. Later documents describe the development of a lyophilized formulation comprising full length humanized antibody huMAb4D5-8 described in WO 92/22653. Herceptin® trastuzumab is currently approved by the FDA for the treatment of metastatic breast cancer that overexpresses HER2—(1) as a single agent after previous treatment of the metastatic breast cancer with one or more chemotherapy regimens and (2) in combination with paclitaxel in such patients without prior chemotherapy for their metastatic breast cancer. Moreover, there is evidence that the addition of trastuzumab to taxane adjuvant or neoadjuvant chemotherapy improves to patients with earlier stage breast cancer.

HKI-272, (E)-N-{4-[3-chloro-4-(2-pyridinyl methoxy)anilino]-3-cyano-7-ethoxy-6-quinolinyl}-4-(dimethylamino)-2-butenamide, has been described as a promising anticancer drug candidate for the treatment of breast cancers and other HER-2-dependent cancers. Because it also inhibits the EGFR kinase with similar potency, HKI-272 may be useful to treat tumors that overexpress both HER-2 and EGFR and be more efficacious than a specific EGFR or HER-2 antagonist. S. K. Rabindran et al, "Antitumor Activity of HKI-272, an Orally Active, Irreversible Inhibitor of the HER-2 Tyrosine Kinase", Cancer Research 64, 3958-3965, Jun. 1, 2004. See, U.S. Pat. No. 6,288,082; 6,297,258.

What is needed is an improved antineoplastic therapy.

DETAILED DESCRIPTION OF THE INVENTION

Figure 1:
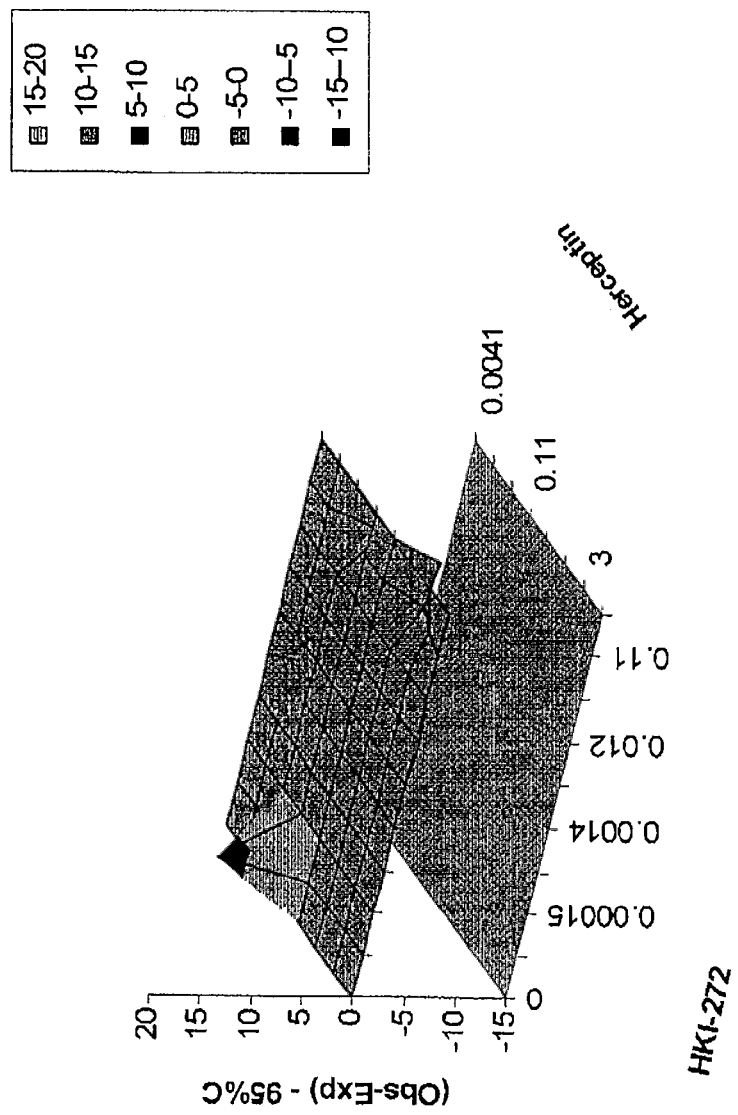
FIG. 1 is a 3-dimensional contour plot with the plane at 0% representing additive interaction, and peaks and valleys representing areas of synergy or antagonism, respectively, between the Herceptin® trastuzumab ("Herceptin") and HKI-272 in BT474 [HER-2+ (amplified); ATCC HTB-20] cells.

This invention provides the use of combinations comprising a trastuzumab, an mTOR inhibitor and/or a HKI-272 in the treatment of neoplasms. Thus, the invention provides for the combined use of a trastuzumab with an mTOR inhibitor, the combined use of trastuzumab with a HKI-272, the combined use of an mTOR inhibitor with a HKI-272, or the combined use of a trastuzumab with mTOR inhibitor and a HKI-272. The invention further provides products containing a trastuzumab in combination with an mTOR inhibitor and/or a HKI-272 formulated for simultaneous, separate or sequential use in treating neoplasms in a mammal. The invention is also useful as an adjuvant and/or neoadjuvant therapy of earlier stages of breast cancer. The following detailed description illustrates temsirolimus. However, other mTOR inhibitors may be substituted for temsirolimus in the methods, combinations and products described herein.

These methods, combinations and products are useful in the treatment of a variety of neoplasms associated with overexpression or amplification of HER2, including, for example, lung cancers, including bronchioalveolar carcinoma and non small cell lung cancer, breast cancers, prostate cancers, myeloma, head and neck cancer, or transitional cell carcinoma; small cell and large cell neuroendocrine carcinoma of the uterine cervix.

In one embodiment, the combination of temsirolimus and trastuzumab is particularly well suited for treatment of metastatic breast cancer. In another embodiment, the combination of trastuzumab and an mTOR inhibitor and/or a HKI-272, are well suited for treatment of neoplasms (breast, kidney, bladder, mouth, larynx, esophagus, stomach, colon, ovary, and lung), and polycystic kidney disease.

As used herein, the term mTOR inhibitor means a compound or ligand, or a pharmaceutically acceptable salt thereof, that inhibits cell replication by blocking the progression of the cell cycle from G1 to S. The term includes the neutral tricyclic compound rapamycin (sirolimus) and other rapamycin compounds, including, e.g., rapamycin derivatives, rapamycin analogues, other macrolide compounds that inhibit mTOR activity, and all compounds included within the definition below of the term "a rapamycin". These include compounds with a structural similarity to "a rapamycin", e.g., compounds with a similar macrocyclic structure that have been modified to enhance therapeutic benefit. FK-506 can also be used in the method of the invention.

As used herein, the term a rapamycin defines a class of immunosuppressive compounds that contain the basic rapamycin nucleus as shown below.

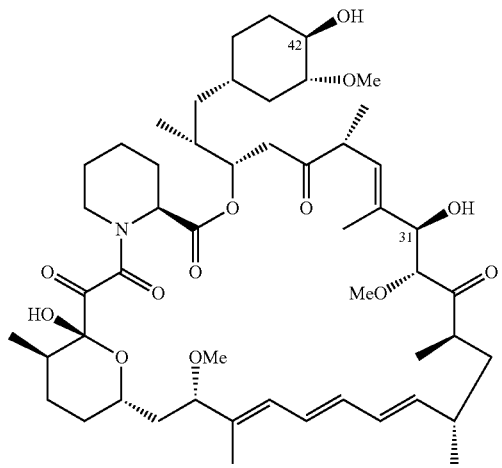 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](O)[C@H](OC)C2)CC(=O)[C@H](C)/C=C(\C)[C@@H](O)[C@@H](OC)C(=O)[C@H](C)C[C@H](C)/C=C/C=C/C=C/1C]

The rapamycins of this invention include compounds that are chemically or biologically modified as derivatives of the rapamycin nucleus, while still retaining immunosuppressive properties. Accordingly, the term a rapamycin includes rapamycin, and esters, ethers, carbamates, oximes, hydrazones, and hydroxylamines of rapamycin, as well as rapamycins in which functional groups on the rapamycin nucleus have been modified, for example through reduction or oxidation. Also included in the term a rapamycin are pharmaceutically acceptable salts of rapamycins.

The term a rapamycin also includes 42- and/or 31-esters and ethers of rapamycin as described in the following patents, which are all hereby incorporated by reference: alkyl esters (U.S. Pat. No. 4,316,885); aminoalkyl esters (U.S. Pat. No. 4,650,803); fluorinated esters (U.S. Pat. No. 5,100,883); amide esters (U.S. Pat. No. 5,118,677); carbamate esters (U.S. Pat. No. 5,118,678); silyl esters (U.S. Pat. No. 5,120,842); aminodiesters (U.S. Pat. No. 5,162,333); sulfonate and sulfate esters (U.S. Pat. No. 5,177,203); esters (U.S. Pat. No. 5,221,670); alkoxyesters (U.S. Pat. No. 5,233,036); O-aryl, -alkyl, -alkenyl, and -alkynyl ethers (U.S. Pat. No. 5,258,389); carbonate esters (U.S. Pat. No. 5,260,300); arylcarbonyl and alkoxycarbonyl carbamates (U.S. Pat. No. 5,262,423); carbamates (U.S. Pat. No. 5,302,584); hydroxyesters (U.S. Pat. No. 5,362,718); hindered esters (U.S. Pat. No. 5,385,908); heterocyclic esters (U.S. Pat. No. 5,385,909); gem-disubstituted esters (U.S. Pat. No. 5,385,910); amino alkanoic esters (U.S. Pat. No. 5,389,639); phosphorylcarbamate esters (U.S. Pat. No. 5,391,730); carbamate esters (U.S. Pat. No. 5,411,967); carbamate esters (U.S. Pat. No. 5,434,260); amidino carbamate esters (U.S. Pat. No. 5,463,048); carbamate esters (U.S. Pat. No. 5,480,988); carbamate esters (U.S. Pat. No. 5,480,989); carbamate esters (U.S. Pat. No. 5,489,680); hindered N-oxide esters (U.S. Pat. No. 5,491,231); biotin esters (U.S. Pat. No. 5,504,091); O-alkyl ethers (U.S. Pat. No. 5,665,772); and PEG esters of rapamycin (U.S. Pat. No. 5,780,462). The preparation of these esters and ethers is disclosed in the patents listed above.

Further included within the definition of the term a rapamycin are 27-esters and ethers of rapamycin, which are disclosed in U.S. Pat. No. 5,256,790. Also described are C-27 ketone rapamycins which are reduced to the corresponding alcohol, which is in turn converted to the corresponding ester or ether. The preparation of these esters and ethers is disclosed in the patent listed above. Also included are oximes, hydrazones, and hydroxylamines of rapamycin are disclosed in U.S. Pat. Nos. 5,373,014, 5,378,836, 5,023,264, and 5,563,145. The preparation of these oximes, hydrazones, and hydroxylamines is disclosed in the above-listed patents. The preparation of 42-oxorapamycin is disclosed in U.S. Pat. No. 5,023,263.

As used herein, the term a CCI-779 means rapamycin 42-ester with 3-hydroxy-2-(hydroxymethyl)-2-methylpropionic acid (temsirolimus), and encompasses prodrugs, derivatives, pharmaceutically acceptable salts, or analogs thereof.

Examples of a rapamycin include, e.g., rapamycin, 32-deoxorapamycin, 16-pent-2-ynyloxy-32-deoxorapamycin, 16-pent-2-ylyloxy-32(S)-dihydro-rapamycin, 16-pent-2-ylyloxy-32(S)-dihydro-40-O-(2-hydroxyethyl)-rapamycin, 40-O-(2-hydroxyethyl)-rapamycin, rapamycin 42-ester with 3-hydroxy-2-(hydroxymethyl)-2-methylpropionic acid (CCI-779), 40-[3-hydroxy-2-(hydroxymethyl)-2-methylpropanoate]-rapamycin, or a pharmaceutically acceptable salt thereof, as disclosed in U.S. Pat. No. 5,362,718, ABT578, or 40-(tetrazolyl)-rapamycin, 40-epi-(tetrazolyl)-rapamycin, e.g., as disclosed in International Patent Publication No. WO 99/15530, or rapamycin analogs as disclosed in International Patent Publication No. WO 98/02441 and WO 01/14387, e.g., AP23573. In another embodiment, the compound is Certican™ everolimus (42-O-(2-hydroxy)ethyl rapamycin), Novartis, U.S. Pat. No. 5,665,772.

As used herein, a HKI-272 refers to a compound having the following core,

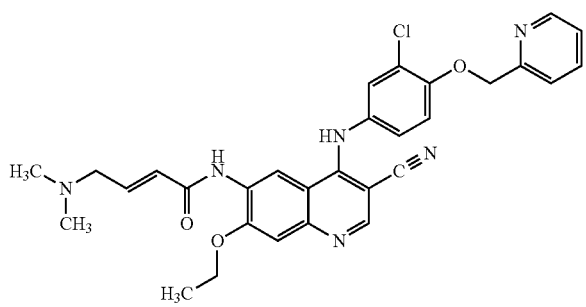 [SMILES: CCOc1cc2ncc(C#N)c(Nc3ccc(OCc4ccccn4)c(Cl)c3)c2cc1NC(=O)/C=C/CN(C)C]

or a derivative or pharmaceutically acceptable salt thereof. Suitable derivatives may include, e.g., an ester, ether, or carbamate. The core structure, HKI-272, has the chemical name (E)-N-{4-[3-chloro-4-(2-pyridinylmethoxy) anilino]-3-cyano-7-ethoxy-6-quinolinyl}-4-(dimethylamino)-2-butenamide.

In one embodiment, the invention also provides for use of substituted 3-cyano quinolines having structure:

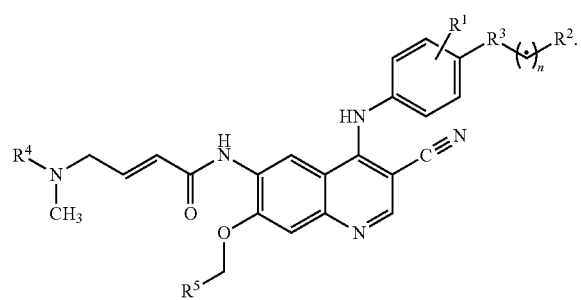

where $R_1$ is halogen;
$R_2$ is pyridinyl, thiophene, pyrimidine, thiazole, or phenyl optionally substituted with up to three substituents;
$R_3$ is —O— or —S—;
$R_4$ is methyl or $CH_2CH_2OCH_3$;
$R_5$ is ethyl or methyl; and
n is 0 or 1.

These compounds, of which HKI-272 is a species, are characterized by the ability to act as potent HER-2 inhibitors. See, e.g., U.S. Pat. Nos. 6,288,082 and 6,297,258. These compounds and their preparation are described in detail in US Published Patent Application No. 2005/0059678. For convenience, HKI-272 is used throughout this specification. However, it will be understood that the compound of the structure provided above can be substituted for HKI-272 in the combinations with an mTOR inhibitor and/or a trastuzumab which are described in detail below.

The following standard pharmacological test procedure can be used to determine whether a compound is an mTOR inhibitor, as defined herein. Treatment of growth factor stimulated cells with an mTOR inhibitor like rapamycin completely blocks phosphorylation of serine 389 as evidenced by Western blot and as such constitutes a good assay for mTOR inhibition. Thus, whole cell lysates from cells stimulated by a growth factor (e.g., IGF1) in culture in the presence of an mTOR inhibitor should fail to show a band on an acrylamide gel capable of being labeled with an antibody specific for serine 389 of p70s6K.

It is preferred that the mTOR inhibitor used in the antineoplastic combinations of this invention is a rapamycin, and more preferred that the mTOR inhibitor is rapamycin, temsirolimus, or everolimus. The preparation of everolimus is described in U.S. Pat. No. 5,665,772.

The preparation of temsirolimus is described in U.S. Pat. No. 5,362,718. A regiospecific synthesis of temsirolimus is described in U.S. Pat. No. 6,277,983, which is hereby incorporated by reference. Still another regiospecific method for synthesis of temsirolimus is described in US Patent Publication No. 2005-0033046-A1, published Feb. 10, 2005 (application Ser. No. 10/903,062, filed Jul. 30, 2004), and its counterpart, International Patent Publication No. WO 2005/016935, published Apr. 7, 2005.

Trastuzumab, and methods of making and formulating same have been described. See, e.g., U.S. Pat. Nos. 6,821,515; 6,399,063 and 6,387,371. Trastuzumab is available commercially from Genentech. As used herein, the term a trastuzumab includes trastuzumab and altered forms of, and derivatives of, trastuzumab. The term a trastuzumab includes agents that target the same epitope on the Her-2 receptor as targeted by trastuzumab. The epitope is known from H. S. Cho et al., Structure of the extracellular region of HER2 alone and in complex with the trastuzumab Fab, *Nature* 421 (2003), pp. 756-760.

HKI-272 and methods of making and formulating same have been described. See, e.g., US Published Patent Application No. 2005/0059678; U.S. Pat. No. 6,002,008, can also be used to prepare the substituted 3-quinoline compounds used this invention and are hereby incorporated by reference. In addition to the methods described in these documents, WO-9633978 and WO-9633980 describe methods that are useful for the preparation of these compounds. Although these methods describe the preparation of certain quinazolines, they are also applicable to the preparation of correspondingly substituted 3-cyanoquinolines and are hereby incorporated by reference.

As used in accordance with this invention, the term "treatment" means treating a mammal having a neoplasm by providing said mammal an effective amount of a combination of a two or three-way combination of the components selected from an mTOR inhibitor, a trastuzumab and/or a HKI-272 with the purpose of inhibiting progression of the neoplastic disease, growth of a tumor in such mammal, eradication of the neoplastic disease, prolonging survival of the mammal and/or palliation of the mammal.

As used in accordance with this invention, the term "providing," with respect to providing an mTOR inhibitor with a trastuzumab and/or a HKI-272, means either directly administering the mTOR inhibitor, or administering a prodrug, derivative, or analog which will form an effective amount of the mTOR inhibitor within the body, along with a trastuzumab and/or a HKI-272 directly, or administering a prodrug, derivative, or analog which will form an effective amount of a trastuzumab or a HKI-272 in the body.

Use of a combination of an mTOR inhibitor (e.g., temsirolimus), a trastuzumab and/or a HKI-272 also provides for the use of combinations of each of the agents in which one, two, or all three agents is used at subtherapeutically effective dosages. Subtherapeutically effective dosages may be readily determined by one of skill in the art, in view of the teachings herein. In one embodiment, the subtherapeutically effective dosage is a dosage which is effective at a lower dosage when used in the combination regimen of the invention, as compared to the dosage that is effective when used alone. The invention further provides for one or more of the active agents in the combination of the invention to be used in a supratherapeutic amount, i.e., at a higher dosage in the combination than when used alone. In this embodiment, the other active agent(s) may be used in a therapeutic or subtherapeutic amount.

The combinations of the invention may be in the form of a kit of parts. The invention therefore includes a product containing an mTOR inhibitor, a trastuzumab and/or a HKI-272 as a combined preparation for simultaneous, separate or sequential delivery for the treatment of a neoplasm in a mammal in need thereof. In one embodiment, a product contains temsirolimus and a trastuzumab as a combined preparation for simultaneous, separate or sequential use in treating a neoplasm in a mammal in need thereof. Optionally, the product further contains a HKI-272. HKI-272 may be separately formulated, e.g., for oral delivery. In another embodiment, a product contains temsirolimus and a HKI-272 as a combined preparation for simultaneous, separate or sequential use in a neoplasm in a mammal in need thereof. Optionally, the product further contains a trastuzumab. In yet another embodiment, the product contains a trastuzumab and a HKI-272. Optionally, the product further contains an mTOR inhibitor. In one embodiment, the neoplasm is metastatic breast cancer.

In one embodiment, a pharmaceutical pack contains a course of treatment of a neoplasm for one individual mammal, wherein the pack contains units of an mTOR inhibitor in unit dosage form and units of a trastuzumab in unit dosage form, optionally further in combination with units of a HKI-272 in unit dosage form. In another embodiment, a pharmaceutical pack contains a course of treatment of a neoplasm for one individual mammal, wherein the pack contains units of an mTOR inhibitor in unit dosage form and units of a HKI-272 in unit dosage form, optionally further in combination with units of a trastuzumab in unit dosage form. In yet another embodiment, a pharmaceutical pack contains a course of treatment of a neoplasm for one individual mammal, wherein the pack contains units of a trastuzumab in unit dosage form and units of a HKI-272 in unit dosage form, optionally further in combination with units of an mTOR inhibitor in unit dosage form. In one embodiment, a pharmaceutical pack as described herein contains a course of treatment of metastatic breast cancer for one individual mammal.

Administration of the compositions may be oral, intravenous, respiratory (e.g., nasal or intrabronchial), infusion, parenteral (besides i.v., such as intralesional, intraperitoneal and subcutaneous injections), intraperitoneal, transdermal (including all administration across the surface of the body and the inner linings of bodily passages including epithelial and mucosal tissues), and vaginal (including intrauterine administration). Other routes of administration are also feasible, such as via liposome-mediated delivery; topical, nasal, sublingual, uretheral, intrathecal, ocular or otic delivery, implants, rectally, intranasally.

While the components of the invention may be delivered via the same route, a product or pack according to the invention may contain a rapamycin, such as temsirolimus, for delivery by a different route than that of the trastuzumab or the HKI-272, e.g., one or more of the components may be delivered orally, while one or more of the others are administered intravenously. In one embodiment, temsirolimus is prepared for oral delivery, a HKI-272 is prepared for oral delivery and trastuzumab is prepared for intravenous delivery. In another embodiment, both temsirolimus and a trastuzumab are prepared for intravenous delivery. In still another embodiment, all of the components are prepared for oral delivery. Optionally, other active components may be delivered by the same or different routes as the mTOR inhibitor (e.g., temsirolimus) or trastuzumab. Other variations would be apparent to one skilled in the art and are contemplated within the scope of the invention.

The mTOR inhibitor plus trastuzumab combination may be administered in the absence of a HKI-272. In one embodiment, these are the sole active antineoplastic agents utilized in the regimen. In another embodiment, the mTOR inhibitor/trastuzumab combination is administered in combination with HKI-272.

The mTOR inhibitor plus HKI-272 combination may be administered in the absence of trastuzumab. In another embodiment, the mTOR inhibitor/HKI-272 combination is administered in combination with trastuzumab. In one embodiment, these two and three-way combinations are the sole active antineoplastic agents utilized in the regimen. In another embodiment, these two and three-way combinations may be utilized in further combination with other active agents.

The trastuzumab plus HKI-272 combination may be administered in the absence of an mTOR inhibitor. In another embodiment, the trastuzumab/HKI-272 combination is administered in combination with an mTOR inhibitor. In one embodiment, these two and three-way combinations are the sole active antineoplastic agents utilized in the regimen. In another embodiment, these two and three-way combinations may be utilized in further combination with other active agents.

As is typical with oncology treatments, dosage regimens are closely monitored by the treating physician, based on numerous factors including the severity of the disease, response to the disease, any treatment related toxicities, age, and health of the patient. Dosage regimens are expected to vary according to the route of administration.

It is projected that initial i.v. infusion dosages of the mTOR inhibitor (e.g., temsirolimus) will be from about 5 to about 175 mg, or about 5 to about 25 mg, when administered on a weekly dosage regimen. It is projected that the oral dosage of an mTOR useful in the invention will be 10 mg/week to 250 mg/week, about 20 mg/week to about 150 mg/week, about 25 mg/week to about 100 mg/week, or about 30 mg/week to about 75 mg/week. For rapamycin, the projected oral dosage will be between 0.1 mg/day to 25 mg/day. Precise dosages will be determined by the administering physician based on experience with the individual subject to be treated.

Other dosage regimens and variations are foreseeable, and will be determined through physician guidance. It is preferred that the mTOR inhibitor is administered by i.v. infusion or orally, preferably in the form of tablets or capsules.

For trastuzumab, single doses and multiple doses are contemplated. In one embodiment, a single loading dose of trastuzumab is administered as a 90-minute intravenous infusion in a range of about 4-5 mg/kg on day 1, followed by about 2 mg/kg per week starting on day 8. Typically, 3 weeks is 1 cycle. From 1, to 2 to 3, weeks may be provided between cycles. Trastuzumab may also be given at a dose of 6 mg/kg once every 3-4 weeks. In addition, trastuzumab may also be given after completion of chemotherapy as maintenance therapy.

For a HKI-272, it is desired that a compound of the invention is in the form of a unit dose. Suitable unit dose forms include tablets, capsules and powders in sachets or vials. Such unit dose forms may contain from 0.1 to 300 mg of a compound of the invention and preferably from 2 to 100 mg. Still further preferred unit dosage forms contain 5 to 50 mg of a compound of the present invention. The compounds of the present invention can be administered at a dose range of about 0.01 to 100 mg/kg or preferably at a dose range of 0.1 to 10 mg/kg. In one embodiment, the compounds are administered orally from 1 to 6 times a day, more usually from 1 to 4 times a day. Alternatively, the compounds may be administered through another suitable route, e.g., intravenous. In still another embodiment, the compounds are administered once a week. In certain situations, dosing with the HKI-272 may be delayed or discontinued for a brief period (e.g., 1, 2 or three weeks) during the course of treatment. Such a delay or discontinuation may occur once, or more, during the course of treatment. The effective amount will be known to one of skill in the art; it will also be dependent upon the form of the compound. One of skill in the art could routinely perform empirical activity tests to determine the bioactivity of the compound in bioassays and thus determine what dosage to administer.

These regimens may be repeated, or alternated, as desired. Other dosage regimens and variations are foreseeable, and will be determined through physician guidance.

For example, in one embodiment, the regimen further comprises administration of a taxane, e.g., docetaxel and paclitaxel [e.g., a suspension of paclitaxel bound to albumen nanoparticles, which is available as Abraxane]. Paclitaxel may also be administered on a weekly schedule, at doses 60-100 mg/m2 administered over 1 hour, weekly, or 2-3 weekly doses followed by a one week rest. In one embodiment, paclitaxel is administered intravenously over 3 hours at a dose of 175 mg/m$^2$, optionally followed by cisplatin at a dose of 75 mg/m$^2$; or paclitaxel administered intravenously over 24 hours at a dose of 135 mg/m$^2$, optionally followed by cisplatin at a dose of 75 mg/m$^2$. In patients previously treated with therapy for carcinoma, paclitaxel can be injected at several doses and schedules. However, the optimal regimen is not yet clear. The recommended regimen is paclitaxel 135 mg/m$^2$ or 175 mg/m$^2$ administered intravenously over 3 hours every 3 weeks. These doses may be altered as needed or desired.

Still other active agents may be included in a combination with an mTOR inhibitor and a trastuzumab, including, e.g., chemotherapeutic agents, such as alkylating agents; hormonal agents (i.e., estramustine, tamoxifen, toremifene, anastrozole, or letrozole); antibiotics (i.e., plicamycin, bleomycin, mitoxantrone, idarubicin, dactinomycin, mitomycin, or daunorubicin); antimitotic agents (i.e., vinblastine, vincristine, teniposide, or vinorelbine, available as Navelbine); topoisomerase inhibitors (i.e., topotecan, irinotecan, etoposide, or doxorubicin, e.g., CAELYX or Doxil, pegylated liposomal doxorubicin hydrochloride); and other agents (i.e., hydroxyurea, altretamine, rituximab, paclitaxel, docetaxel, L-asparaginase, or gemtuzumab ozogamicin); biochemical modulating agents, imatib, EGFR inhibitors such as EKB-569 or other multi-kinase inhibitors, e.g., those that targets serine/threonine and receptor tyrosine kinases in both the tumor cell and tumor vasculature, or immunomodulators (i.e., interferons, IL-2, or BCG). Examples of suitable interferons include interferon α, interferon β, interferon γ, and mixtures thereof.

In one embodiment, the combination of an mTOR inhibitor and a trastuzumab may be further combined with antineoplastic alkylating agents, e.g., those described in US 2002-0198137A1. Antineoplastic alkylating agents are roughly classified, according to their structure or reactive moiety, into several categories which include nitrogen mustards, such as MUSTARGEN (mechlorethamine), cyclophosphamide, ifosfamide, melphalan, and chlorambucil; azidines and epoxides, such as thiotepa, mitomycin C, dianhydrogalactitol, and dibromodulcitol; alkyl sulfinates, such as busulfan; nitrosoureas, such as bischloroethylnitrosourea (BCNU), cyclohexyl-chloroethylnitrosourea (CCNU), and methylcyclohexylchloroethylnitrosourea (MeCCNU); hydrazine and triazine derivatives, such as procarbazine, dacarbazine, and temozolomide; streptazoin, melphalan, chlorambucil, carmustine, methclorethamine, lomustine) and platinum compounds. Platinum compounds are platinum containing agents that react preferentially at the N7 position of guanine and adenine residues to form a variety of monofunctional and bifunctional adducts. (Johnson S W, Stevenson J P, O'Dwyer P J. Cisplatin and Its Analogues. In Cancer Principles & Practice of Oncology 6$^{th}$ Edition. ed. DeVita V T, Hellman S, Rosenberg S A. Lippincott Williams & Wilkins. Philadelphia 2001. p. 378.) These compounds include cisplatin, carboplatin, platinum IV compounds, and multinuclear platinum complexes.

The following are representative examples of alkylating agents of this invention. Mechlorethamine is commercially available as an injectable (MUSTARGEN). Cyclophosphamide is commercially available as an injectable (cyclophosphamide, lyophilized CYTOXAN, or NEOSAR) and in oral tablets (cyclophosphamide or CYTOXAN). Ifosfamide is commercially available as an injectable (IFEX). Melphalan is commercially available as an injectable (ALKERAN) and in oral tablets (ALKERAN). Chlorambucil is commercially available in oral tablets (LEUKERAN). Thiotepa is commercially available as an injectable (thiotepa or THIOPLEX). Mitomycin is commercially available as an injectable (mitomycin or MUTAMYCIN). Busulfan is commercially available as an injectable (BUSULFEX) and in oral tablets (MYLERAN). Lomustine (CCNU) is commercially available in oral capsules (CEENU). Carmustine (BCNU) is commercially available as an intracranial implant (GLIADEL) and as an injectable (BICNU). Procarbazine is commercially available in oral capsules (MATULANE). Temozolomide is commercially available in oral capsules (TEMODAR). Cisplatin is commercially available as an injectable (cisplatin, PLATINOL, or PLATINOL-AQ). Carboplatin is commercially available as an injectable (PARAPLATIN). Oxiplatin is commercially available as ELOXATIN.

In another embodiment, a combination of the invention may further include treatment with an antineoplastic antimetabolite, such as is described in US Patent Publication No. US 2005-0187184A1 or US 2002-0183239 A1. As used in accordance with this invention, the term "antimetabolite" means a substance which is structurally similar to a critical natural intermediate (metabolite) in a biochemical pathway leading to DNA or RNA synthesis which is used by the host in that pathway, but acts to inhibit the completion of that pathway (i.e., synthesis of DNA or RNA). More specifically, antimetabolites typically function by (1) competing with metabolites for the catalytic or regulatory site of a key enzyme in DNA or RNA synthesis, or (2) substitute for a metabolite that is normally incorporated into DNA or RNA, and thereby producing a DNA or RNA that cannot support replication. Major categories of antimetabolites include (1) folic acid analogs, which are inhibitors of dihydrofolate reductase (DHFR); (2) purine analogs, which mimic the natural purines (adenine or guanine) but are structurally different so they competitively or irreversibly inhibit nuclear processing of DNA or RNA; and (3) pyrimidine analogs, which mimic the natural pyrimidines (cytosine, thymidine, and uracil), but are structurally different so thy competitively or irreversibly inhibit nuclear processing of DNA or RNA.

The following are representative examples of antimetabolites of this invention. 5-Fluorouracil (5-FU; 5-fluoro-2,4 (1H,3H)-pyrimidinedione) is commercially available in a topical cream (FLUOROPLEX or EFUDEX), a topical solution (FLUOROPLEX or EFUDEX), and as an injectable containing 50 mg/mL 5-fluorouracil (ADRUCIL or fluorouracil). Floxuradine (2'-deoxy-5-fluorouridine) is commercially available as an injectable containing 500 mg/vial of floxuradine (FUDR or floxuradine). Thioguanine (2-amino-1,7-dihydro-6-H-purine-6-thione) is commercially available in 40 mg oral tablets (thioguanine). Cytarabine (4-amino-1-(beta)-D-arabinofuranosyl-2(1H)-pyrimidinone) is commercially available as a liposomal injectable containing 10 mg/mL cytarabine (DEPOCYT) or as a liquid injectable containing between 1 mg-1 g/vial or 20 mg/mL (cytarabine or CYTOSAR-U). Fludarabine (9-H-Purin-6-amine,2-fluoro-9-(5-O-phosphono-(beta)-D-a-rabinofuranosyl) is commercially available as a liquid injectable containing 50 mg/vial (FLUDARA). 6-Mercaptopurine (1,7-dihydro-6H-purine-6-thione) is commercially available in 50 mg oral tablets (PURINETHOL). Methotrexate (MTX; N-[4-[[(2,4-diamino-6-pteridinyl)methyl]methylamino]benzoyl]-L-glutamic acid) is commercially available as a liquid injectable containing between 2.5-25 mg/mL and 20 mg-1 g/vial (methotrexate sodium or FOLEX) and in 2.5 mg oral tablets (methotrexate sodium). Gemcitabine (2'-deoxy-2',2'-difluorocytidine monohydrochloride ((beta)-isomer)), is commercially available as a liquid injectable containing between 200 mg-1 g/vial (GEMZAR). Capecitabine (5'-deoxy-5-fluoro-N-[(pentyloxy)carbonyl]-cytidine) is commercially available as a 150 or 500 mg oral tablet (XELODA). Pentostatin ((R)-3-(2-deoxy-(beta)-D-erythro-pentofuranosyl)-3,6,7,-8-tetrahydroimidazo[4,5-d][1,3]diazepin-8-ol) is commercially available as a liquid injectable containing 10 mg/vial (NIPENT). Trimetrexate (2,4-diamino-5-methyl-6-[(3,4,5-trimethoxyanilino)methyl]quinazoline mono-D-glucuronate) is commercially available as a liquid injectable containing between 25-200 mg/vial (NEUTREXIN). Cladribine (2-chloro-6-amino-9-(2-deoxy-(beta)-D-erythropento-furanosyl) purine) is commercially available as a liquid injectable containing 1 mg/mL (LEUSTATIN).

The term "biochemical modulating agent" is well known and understood to those skilled in the art as an agent given as an adjunct to anti-cancer therapy, which serves to potentate its antineoplastic activity, as well as to counteract the side effects of the active agent, e.g., an antimetabolite. Leucovorin and levofolinate are typically used as biochemical modulating agents for methotrexate and 5-FU therapy. Leucovorin (5-formyl-5,6,7,8-tetrahydrofolic acid) is commercially available as an injectable liquid containing between 5-10 mg/mL or 50-350 mg/vial (leucovorin calcium or WELLCOVORIN) and as 5-25 mg oral tablets (leucovorin calcium). Levofolinate (pharmacologically active isomer of 5-formyltetrahydrofolic acid) is commercially available as an injectable containing 25-75 mg levofolinate (ISOVORIN) or as 2.5-7.5 mg oral tablets (ISOVORIN).

In another embodiment, the combination of the invention further includes an active agent selected from among a kinase inhibitor. Particularly desirable are multi-kinase inhibitors target serine/threonine and receptor tyrosine kinases in both the tumor cell and tumor vasculature. Examples of suitable kinase inhibitors are Sorafenib (BAY 43-9006, Bayer, commercially available as NEXAVAR), which has been granted Fast Track status by the FDA for metastatic renal cell cancer. Another suitable farnesyltransferase inhibitor is Zarnestra (R115777, tipifarnib). Yet another compound is suntinib (SUTENT). Still other suitable compounds that target Ras/Raf/MEK and/or MAP kinases include, e.g., avastin, ISIS 5132, and MEK inhibitors such as CI-1040 or PD 0325901.

As described herein, subtherapeutically effective amounts of trastuzumab and temsirolimus may be used to achieve a therapeutic effect when administered in combination. For example, trastuzumab may be provided at dosages of 5 to 50% lower, 10 to 25% lower, or 15 to 20% lower, when provided along with temsirolimus. For example, a resulting trastuzumab dosage can be from about 8 to 40 mg, or about 8 to 30 mg, or 8 to 25 mg. Subtherapeutically effective amounts of trastuzumab are expected to reduce the side-effects of trastuzumab treatment. The invention further provides for one or more of the active agents in the combination of the invention to be used in a supratherapeutic amount, i.e., at a higher dosage in the combination than when used alone. In this embodiment, the other active agent(s) may be used in a therapeutic or subtherapeutic amount.

The mTOR inhibitor, trastuzumab, HKI-272 or other active compounds used in the combination and products of the invention may be formulated in any suitable manner. For example, oral formulations containing the mTOR inhibitor (and optionally, other active compounds) useful in combination and products of this invention may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Preferred surface modifying agents include nonionic and anionic surface modifying agents. Representative examples of surface modifying agents include, but are not limited to, poloxamer 188, benzalkonium chloride, calcium stearate, cetostearyl alcohol, cetomacrogol emulsifying wax, sorbitan esters, colloidal silicon dioxide, phosphates, sodium dodecylsulfate, magnesium aluminum silicate, and triethanolamine. Oral formulations herein may utilize standard delay or time release formulations to alter the absorption of the active compound(s). The oral formulation may also consist of administering the active ingredient in water or a fruit juice, containing appropriate solubilizers or emulsifiers as needed. Preferred oral formulations for rapamycin 42-ester with 3-hydroxy-2-(hydroxymethyl)-2-methylpropionic acid are described in US Patent Publication No. 2004/0077677 A1, published Apr. 22, 2004.

In some cases it may be desirable to administer the compounds directly to the airways in the form of an aerosol.

The compounds may also be administered parenterally or intraperitoneally. Solutions or suspensions of these active compounds as a free base or pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils. Preferred injectable formulations for rapamycin 42-ester with 3-hydroxy-2-(hydroxymethyl)-2-methylpropionic acid are described in US Patent Publication No. 2004/0167152 A1, published Aug. 26, 2004.

For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Transdermal administration may be accomplished through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semi-permeable membrane covering a reservoir containing the active ingredient with or without a carrier, or a matrix containing the active ingredient. Other occlusive devices are known in the literature.

Suppository formulations may be made from traditional materials, including cocoa butter, with or without the addition of waxes to alter the suppository's melting point, and glycerin. Water soluble suppository bases, such as polyethylene glycols of various molecular weights, may also be used.

As used in this invention, the combination regimen can be given simultaneously or can be given in a staggered regimen, with the mTOR inhibitor being given at a different time during the course of chemotherapy than the trastuzumab. This time differential may range from several minutes, hours, days, weeks, or longer between administration of the at least two agents. Therefore, the term combination (or combined) does not necessarily mean administered at the same time or as a unitary dose, but that each of the components are administered during a desired treatment period. The agents may also be administered by different routes.

Pharmaceutical Packs/Kits:

The invention includes a product or pharmaceutical pack containing a course of an anti-neoplastic treatment for one individual mammal comprising one or more container(s) having one, one to four, or more unit(s) of an mTOR inhibitor (e.g., temsirolimus) in unit dosage form and, optionally, one, one to four, or more unit(s) of a trastuzumab, and optionally, another active agent.

In another embodiment, pharmaceutical packs contain a course of anti-neoplastic treatment for one individual mammal comprising a container having a unit of a rapamycin in unit dosage form, a containing having a unit of trastuzumab, and optionally, a container with another active agent. In other embodiments, the rapamycin is rapamycin, an ester (including a 42-ester, ether (including a 42-ether), oxime, hydrazone, or hydroxylamine of rapamycin. In another embodiment, the rapamycin is 42-O-(2-hydroxy)ethyl rapamycin.

In another embodiment, the rapamycin is temsirolimus, and the pack contains one or more container(s) comprising one, one to four, or more unit(s) of temsirolimus with the components described herein.

In some embodiments, the compositions of the invention are in packs in a form ready for administration. In other embodiments, the compositions of the invention are in concentrated form in packs, optionally with the diluent required to make a final solution for administration. In still other embodiments, the product contains a compound useful in the invention in solid form and, optionally, a separate container with a suitable solvent or carrier for the compound useful in the invention.

In still other embodiments, the above packs/kits include other components, e.g., instructions for dilution, mixing and/or administration of the product, other containers, syringes, needles, etc. Other such pack/kit components will be readily apparent to one of skill in the art.

The following examples illustrate of the uses of the combinations of the invention. It will be readily understood that alterations or modifications, e.g., in the formulation of the components, the routes of delivery, and the dosing, can be made for reasons known to those of skill in the art.

Example 1: Combination Regimen of Temsirolimus (CCI-779) and Trastuzumab in Treatment of Neoplasms Dosing begins at month 1, day 1 with weekly intravenous (IV) temsirolimus and trastuzumab (IV) at the dosages provided below.

Temsirolimus and trastuzumab can be administered simultaneously, consecutively, or on alternative days.

Temsirolimus is administered IV weekly over a 30-minute period using an in-line filter and an automatic dispensing pump. Optionally, antihistamine (diphenhydramine, 25 to 50 mg IV or the equivalent) is administered about 30 minutes prior to temsirolimus infusion.

A trastuzumab loading dose is administered IV weekly over a 90 minute period. Weekly doses are administered, which are typically half the amount of the loading dose. For example, a 4 mg/kg loading dose is typically followed by 2 mg/kg weekly doses. These amounts may be adjusted. In one embodiment, no loading dose is required and the same dose is administered throughout the course of treatment.

| Trastuzumab (mg/kg) | Temsirolimus Dose (mg) |
|---|---|
| 2 | 15 |
| 4 | 25 |
| 6 | 50 |

Dose adjustments and/or delays for temsirolimus, and/or trastuzumab are permitted. For example, treatment may continue as described herein for six months, with weekly doses of temsirolimus. The trastuzumab may be provided on a weekly basis for a cycle, e.g., three-weeks. Typically, 2 to 3 weeks is provided between cycles. In certain situations, dosing with the temsirolimus may be delayed or discontinued for a brief period (e.g., 1, 2 or three weeks) during the regimen. Similarly, a cycle of treatment with trastuzumab may be shortened by one or more weeks, lengthened by one or more weeks, or the period between cycles delayed or eliminated. Such a delay or discontinuation may occur once, or more, during the course of treatment.

Example 2: Use of a Combination Regimen of HKI-272 and Temsirolimus (CCI-779) in Treatment of Neoplasms Dosing begins at month 1, day 1 with daily HKI-272 and weekly intravenous (IV) temsirolimus at the dosages provided below.

On month 1, day 1, HKI-272 is administered orally prior to temsirolimus. Temsirolimus is administered following HKI-272, preferably within 30 minutes.

Temsirolimus is administered IV weekly over a 30-minute period using an in-line filter and an automatic dispensing pump. Optionally, antihistamine (diphenhydramine, 25 to 50 mg IV or the equivalent) is administered about 30 minutes prior to temsirolimus infusion.

Thereafter, HKI-272 is taken orally once daily with food, preferably in the morning.

| HKI-272 (mg) | Temsirolimus Dose (mg) |
|---|---|
| 80 | 15 |
| 160 | 25 |
| 240 | 50 |

Dose adjustments and/or delays for HKI-272 and temsirolimus are permitted. For example, treatment may continue as described herein for six months, with daily doses of HKI-272 and weekly doses of temsirolimus. However, in certain situations, dosing with one or both drugs may be delayed or discontinued for a brief period (e.g., 1, 2 or three weeks) during the regimen course of treatment. Such a delay or discontinuation may occur once, or more, during the course of treatment.

Example 3: Use of a Combination Regimen of HKI-272, Temsirolimus (CCI-779), and Trastuzumab in Treatment of Neoplasms Dosing begins at month 1, day 1 with daily HKI-272 and weekly intravenous (IV) temsirolimus and trastuzumab (IV) at the dosages provided below.

On month 1, day 1, HKI-272 is administered orally prior to temsirolimus. Temsirolimus and trastuzumab are administered following HKI-272, preferably within 30 minutes.

Temsirolimus is administered IV weekly over a 30-minute period using an in-line filter and an automatic dispensing pump. Optionally, antihistamine (diphenhydramine, 25 to 50 mg IV or the equivalent) is administered about 30 minutes prior to temsirolimus infusion.

A trastuzumab loading dose is administered IV weekly over a 90 minute period. Weekly doses are administered, which are typically half the amount of the loading dose. For example, a 4 mg/kg loading dose is typically followed by 2 mg/kg weekly doses. These amounts may be adjusted. In one embodiment, no loading dose is required and the same dose is administered throughout the course of treatment.

Thereafter, HKI-272 is taken orally once daily with food, preferably in the morning.

| HKI-272 (mg) | Trastuzumab (mg/kg) | Temsirolimus Dose (mg) |
|---|---|---|
| 80 | 2 | 15 |
| 160 | 4 | 25 |
| 240 | 6 | 50 |

Dose adjustments and/or delays for HKI-272, temsirolimus, and/or trastuzumab are permitted. For example, treatment may continue as described herein for six months, with daily doses of HKI-272 and a weekly dose of temsirolimus. The trastuzumab may be provided on a weekly basis for a cycle, e.g., three weeks. Typically, 2 to 3 weeks is provided between cycles. However, in certain situations, dosing with the HKI-272 and/or temsirolimus may be delayed or discontinued for a brief period (e.g., 1, 2 or three weeks) during the regimen or course of treatment. Such a delay or discontinuation may occur once, or more, during the course of treatment.

Similarly, a cycle of treatment with trastuzumab may be shortened by one or more weeks, lengthened by one or more weeks, or the period between cycles delayed or eliminated. Such a delay or discontinuation may occur once, or more, during the course of treatment.

Example 4: Use of a Combination Regimen of HKI-272 and Trastuzumab in Treatment of Neoplasms The antineoplastic activity of the HKI-272 plus trastuzumab combination was confirmed in in vitro standard pharmacological test procedure. The following briefly describes the procedure used and the results obtained.

The combination was tested in three breast cancer cell lines of differing genotypes. More particularly, BT474 [HER-2+(amplified); ATCC HTB-20] and is highly sensitive to both HKI-272 and trastuzumab. MDA-MB-361 [HER-2$^+$ (non-amplified); adenocarcinoma; ATCC HTB 27] has lower levels of HER-2 without amplification and less sensitive to both trastuzumab and HKI-272. MCF-7 [HER-2$^-$, EGFR−; adenocarcinoma; ATCC HTB22] has no HER-2 and is resistant to both trastuzumab and HKI-272.

Cells from each of these cell lines were incubated in the presence of a range of concentrations (0.0041, 0.012, 0.037, 0.11, 0.33, 0.1, 3 µg/mg) for each drug. The cells were maintained in RPMI 1640 medium (Life Technologies, Inc., Gaithersburg, Md.) supplemented with 10% fetal bovine serum (FBS, Life Technologies) and 50 µg/ml gentamicin (Life Technologies) under 7% $CO_2$ at 37° C. Cells were plated in 96-well microtiter dishes (12,000 cells/well for BT474 Cells, 6000 cells/well MCF-7 Cells and 10,000 cells/well for MDA-MB-361 Cells) in 100 μl RPMI 1640 medium containing 5% FBS and 50 g/ml gentamicin and incubated overnight at 37° C. Compound dilutions were prepared in the same medium, at 2× final concentration, and 100 μl of the drug dilution was added to the cell-containing wells.

Serial dilutions of one compound were prepared in the presence of a fixed dose of a second compound. Alternatively, a checkerboard dilution series was employed. Cells were cultured for three days in the presence of the drugs. Untreated cells were included as controls. The percentage of surviving cells was determined using sulforhodamine B (SRB, Sigma-Aldrich, St Louis, Mo.), a protein binding dye. Cellular protein was precipitated in each well by the addition of 50 μl 50% cold trichloroacetic acid. After 1 hour, the plates were washed extensively in water and dried. SRB dye reagent (0.4% SRB in 1% acetic acid, 80 μl per well) was added and plates were kept at room temperature for ten minutes. Plates were then washed thoroughly in 1% acetic acid and dried. Cell-associated dye was dissolved in 10 mM Tris (150 μl) and the absorbance was read at 540 nm in a microtiter plate reader. The concentration of compound that caused a fixed percentage inhibition of growth was determined by plotting cell survival (relative to untreated cells) against the compound dose.

A model for studying drug interactions has been described by Prichard and Shipman [Antiviral Research. 14:181-206 (1990); Prichard, Minn., et al., 1993. MacSynergy II. Version 1.0. User's manual. University of Michigan, Ann Arbor.] This is a 3-dimensional model: one for each drug and the third for the biological effect. Theoretical additive interactions are calculated from the individual dose-response curves, based on a dissimilar sites model of additivity (Bliss independence). The calculated additive surface, representing predicted cytotoxicity is subtracted from the experimental surface to reveal areas of enhanced toxicity (synergy) or reduced toxicity (antagonism). The resulting surface appears as a horizontal plane at 0% inhibition above the calculated additive surface, if the interaction is additive. Peaks and valleys deviating from this plane are indicative of synergy and antagonism, respectively. MacSynergy II, a Microsoft Excel-based software was used to perform all calculations automatically. This spreadsheet calculates the theoretical additive interactions, and locates and quantifies synergistic or antagonistic interactions that are significant at the 95% confidence levels. The results were plotted as a 3-dimensional plot, or as a contour plot with the plane at 0% representing additive interaction, and peaks and valleys representing areas of synergy or antagonism, respectively, between the two drugs.

For purposes of this study, the Pritchard and Shipman method was modified to allow determination of the combination effects at different levels of statistical significance (p-values 0.05, 0.01, 0.001). A p-value of 0.05 is considered significant. The method of estimating statistical variability within each experiment was also modified. Variability was determined across all compound combinations, whereas in the original version, variability was estimated separately for each compound combination. It is believed that better estimates of the variability are obtained with the modified approach. In general, single points of synergy or antagonism are not considered representative of either synergistic or antagonistic activity. Thus, single point peaks or valleys are disregarded in the analysis. Furthermore, peaks or valleys that occur only along single concentration of one of the compounds are also disregarded, if no synergy or antagonism is observed at the adjacent, flanking concentrations. Finally, all experiments are repeated at least twice and determinations of synergy and antagonism are made by examination of all the data.

Figure 2:
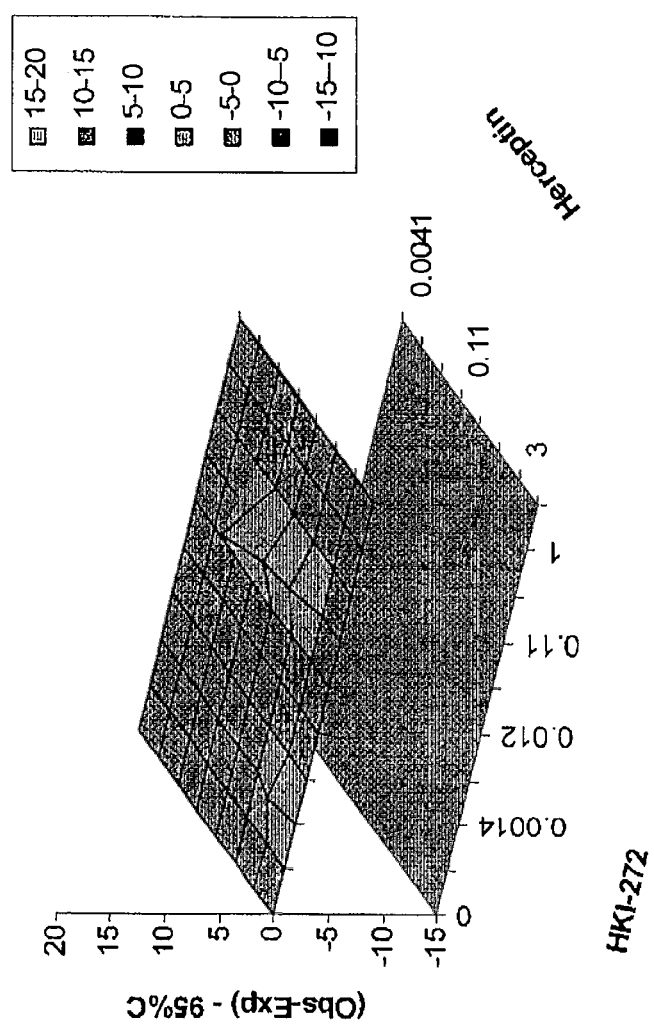
FIG. 2 is a 3-dimensional contour plot with the plane at 0% representing additive interaction, and peaks and valleys representing areas of synergy or antagonism between the Herceptin® trastuzumab ("Herceptin") and HKI-272 in MCF-7 [HER-2$^-$, EGFR–; adenocarcinoma; ATCC HTB22] cells.
Figure 3:
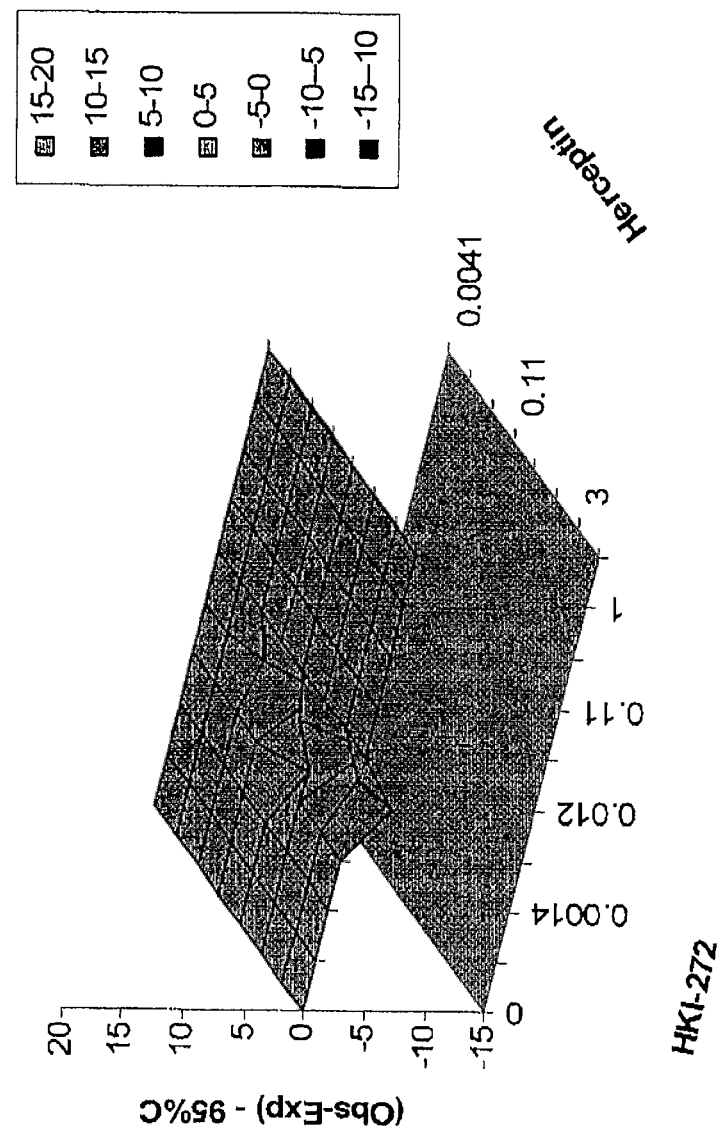
FIG. 3 is a 3-dimensional contour plot with the plane at 0% representing additive interaction, and peaks and valleys representing areas of synergy or antagonism between the Herceptin® trastuzumab ("Herceptin") and HKI-272 in MDA-MB-361 [HER-2$^+$ (non-amplified); adenocarcinoma; ATCC HTB 27] cells.

FIGS. 1-3 provide the results from a single set of experiments. In MDA-MB-361 cells, there is an area of antagonism at 0.11-3 μg/mL trastuzumab for at a concentration of 0.012 μg/mL HK-272 at the 95% confidence level. In MCF7 cells, there is an area of synergy at 0.037-0.33 g/mL trastuzumab for at a concentration of 0.11 μg/mL HKI-272 at the 95% confidence level. For the BT474 cells, there is an area of antagonism at 0.33-1 μg/mL trastuzumab for at a concentration of 0.11 μg/mL HKI-272 at the 95% confidence level. When repeated at the 99% confidence level, no statistically significant areas of antagonism or synergy were found. Based on the above criteria, the combination of trastuzumab and HKI-272 is considered additive across all concentrations.

The results of these standard pharmacological test procedures derived from multiple independent experiments, indicate that combinations of HKI-272 are not significantly antagonistic or synergistic, but are additive over a range of concentrations. These data support the use of the combinations in the treatment of HER2+ cancers. As these combinations contain at least two active antineoplastic agents, the use of such combinations also provides for the use of combinations of each of the agents in which one or both of the agents is used at subtherapeutically effective dosages, thereby lessening toxicity associated with the individual chemotherapeutic agent.

All patents, patent publications, articles, and other documents referenced herein are incorporated by reference. It will be clear to one of skill in the art that modifications can be made to the specific embodiments described herein without departing from the scope of the invention.

The invention claimed is:

1. A method of treating a HER2+ neoplasm in a patient in need thereof, consisting of administering to the patient:
  i) temsirolimus (CCI-779) or a prodrug or pharmaceutically acceptable salt thereof in combination with one or more pharmaceutically acceptable carriers; and
  ii) 0.1 to 300 mg of (E)-N-{4-[3-chloro-4-(2-pyridinylmethoxy)anilino]-3-cyano-7-ethoxy-6-quinolinyl}-4-(dimethylamino)-2-butenamide, or a pharmaceutically acceptable salt thereof, in combination with one or more pharmaceutically acceptable carriers.

2. The method of claim 1, wherein the temsirolimus (CCI-779) and (E)-N-{4-[3-chloro-4-(2-pyridinylmethoxy)anilino]-3-cyano-7-ethoxy-6-quinolinyl}-4-(dimethylamino)-2-butenamide, or pharmaceutically acceptable salt thereof, are administered in subtherapeutically effective amounts.

3. The method of claim 1, wherein the neoplasm is selected from the group consisting of: lung cancer, including bronchioalveolar carcinoma and non small cell lung cancer; breast cancer; myeloma; prostate cancer; head and neck cancer; transitional cell carcinoma; and small cell and large cell neuroendocrine carcinoma of the uterine cervix.

4. The method of claim 3, wherein the breast cancer is metastatic breast cancer.

5. The method of claim 1, wherein the temsirolimus (CCI-779) and (E)-N-{4-[3-chloro-4-(2-pyridinylmethoxy)anilino]-3-cyano-7-ethoxy-6-quinolinyl}-4-(dimethylamino)-2-butenamide, or pharmaceutically acceptable salt thereof, are administered simultaneously, separately, sequentially, or in a staggered regimen to the patient.

6. The method of claim 1, wherein the temsirolimus (CCI-779) and (E)-N-{4-[3-chloro-4-(2-pyridinylmethoxy)

anilino]-3-cyano-7-ethoxy-6-quinolinyl}-4-(dimethylamino)-2-butenamide, or pharmaceutically acceptable salt thereof, are administered to the patient in a formulation suitable for one or more of the following administration routes: oral, as an aerosol, parenteral, intraperitoneal, transdermal, or as a suppository.

7. The method of claim 1, wherein the temsirolimus (CCI-779) and (E)-N-{4-[3-chloro-4-(2-pyridinylmethoxy)anilino]-3-cyano-7-ethoxy-6-quinolinyl}-4-(dimethylamino)-2-butenamide, or pharmaceutically acceptable salt thereof, are administered to the patient using the same route of administration or using different routes of administration.

8. The method of claim 1, wherein the temsirolimus (CCI-779) and (E)-N-{4-[3-chloro-4-(2-pyridinylmethoxy)anilino]-3-cyano-7-ethoxy-6-quinolinyl}-4-(dimethylamino)-2-butenamide, or pharmaceutically acceptable salt thereof, are contained in a pharmaceutical pack or kit.

9. The method of claim 1, wherein the temsirolimus (CCI-779) is administered orally or intravenously.

10. The method of claim 9, wherein an amount in the range of between 10 mg to 250 mg of the temsirolimus (CCI-779) is administered orally to the patient per week.

11. The method of claim 9, wherein an amount in the range of between 5 mg to 175 mg of the temsirolimus (CCI-779) is administered intravenously to the patient per week.

12. The method of claim 11, wherein the (E)-N-{4-[3-chloro-4-(2-pyridinylmethoxy)anilino]-3-cyano-7-ethoxy-6-quinolinyl}-4-(dimethylamino)-2-butenamide, or pharmaceutically acceptable salt thereof, is administered orally.

13. The method of claim 12, wherein the (E)-N-{4-[3-chloro-4-(2-pyridinylmethoxy)anilino]-3-cyano-7-ethoxy-6-quinolinyl}-4-(dimethylamino)-2-butenamide, or pharmaceutically acceptable salt thereof, is administered daily.

14. The method of claim 13, wherein an amount of 80 mg, 160 mg, or 240 mg of the (E)-N-{4-[3-chloro-4-(2-pyridinylmethoxy)anilino]-3-cyano-7-ethoxy-6-quinolinyl}-4-(dimethylamino)-2-butenamide, or pharmaceutically acceptable salt thereof, is administered orally.

* * * * *